US009740921B2

(12) United States Patent
McClure et al.

(10) Patent No.: US 9,740,921 B2
(45) Date of Patent: Aug. 22, 2017

(54) IMAGE PROCESSING SENSOR SYSTEMS

(71) Applicant: TKO Enterprises, Inc., Longmont, CO (US)

(72) Inventors: Neil L. McClure, Longmont, CO (US); Ralph David Wieland, Broomfield, CO (US)

(73) Assignee: TKO Enterprises, Inc., Longmont, CO (US)

(*) Notice: Subject to any disclaimer, the term of this patent is extended or adjusted under 35 U.S.C. 154(b) by 0 days.

(21) Appl. No.: 15/063,402

(22) Filed: Mar. 7, 2016

(65) Prior Publication Data

US 2016/0188965 A1 Jun. 30, 2016

Related U.S. Application Data

(63) Continuation-in-part of application No. 12/916,283, filed on Oct. 29, 2010, now Pat. No. 9,277,878, which is a continuation-in-part of application No. PCT/US2010/025631, filed on Feb. 26, 2010, and a continuation-in-part of application No. 12/481,063, filed on Jun. 9, 2009, now Pat. No. 8,780,198, and a continuation-in-part of application No. 12/481,458,
(Continued)

(51) Int. Cl.
G08B 21/04 (2006.01)
A01M 31/00 (2006.01)
G06K 9/00 (2006.01)
G06K 9/62 (2006.01)
A61B 5/11 (2006.01)
G08B 13/196 (2006.01)

(52) U.S. Cl.
CPC ....... *G06K 9/00335* (2013.01); *A01M 31/002* (2013.01); *A61B 5/1116* (2013.01); *A61B 5/1117* (2013.01); *G06K 9/00342* (2013.01); *G06K 9/627* (2013.01); *G08B 13/1961* (2013.01); *G08B 13/19602* (2013.01); *G08B 13/19663* (2013.01); *G08B 21/043* (2013.01); *G08B 21/0476* (2013.01)

(58) Field of Classification Search
None
See application file for complete search history.

(56) References Cited

U.S. PATENT DOCUMENTS 5,541,934 A 7/1996 Marietta et al.
6,246,321 B1 6/2001 Rechsteiner et al.
(Continued)

FOREIGN PATENT DOCUMENTS

WO  WO 02/41273    5/2002
WO  WO2008139631  11/2008

OTHER PUBLICATIONS

U.S. Appl. No. 12/481,063 Office Action dated Sep. 16, 2011, 13 pages.
(Continued)

*Primary Examiner* — Reza Aghevli
(74) *Attorney, Agent, or Firm* — Fennemore Craig, P.C.

(57) ABSTRACT

An image processing sensor system functions as a stand-alone unit to capture images and process the resulting signals to detect objects or events of interest. The processing significantly improves selectivity and specificity of detection objects and events in a series of motions that may precede a patient who is at elevated risk of falling.

19 Claims, 8 Drawing Sheets

Related U.S. Application Data filed on Jun. 9, 2009, now Pat. No. 9,293,017, and a continuation-in-part of application No. 12/481,483, filed on Jun. 9, 2009, now Pat. No. 9,299,231.

(60) Provisional application No. 61/155,839, filed on Feb. 26, 2009.

(56) References Cited

U.S. PATENT DOCUMENTS

| | | |
|---|---|---|
| 6,359,564 B1 | 3/2002 | Thacker |
| 6,486,778 B2 | 11/2002 | Mahler et al. |
| 6,697,104 B1 | 2/2004 | Yakobi et al. |
| 7,126,476 B2 | 10/2006 | Alkelai et al. |
| 7,161,152 B2 | 1/2007 | DiPoala |
| 7,190,259 B2 | 3/2007 | Kumata et al. |
| 7,200,246 B2 | 4/2007 | Cofer et al. |
| 7,231,654 B2 | 6/2007 | Murai |
| 7,262,697 B2 | 8/2007 | Meng et al. |
| 7,382,405 B2 | 6/2008 | Kusaka et al. |
| 7,414,647 B2 | 8/2008 | Kakou et al. |
| 7,764,218 B2 | 7/2010 | Kruys et al. |
| 2001/0021947 A1 | 9/2001 | Kim |
| 2002/0061134 A1 | 5/2002 | Cofer et al. |
| 2002/0083323 A1 | 6/2002 | Cromer et al. |
| 2003/0048926 A1 | 3/2003 | Watanabe |
| 2003/0169335 A1 | 9/2003 | Monroe |
| 2004/0021947 A1 | 2/2004 | Schofield et al. |
| 2004/0080618 A1 | 4/2004 | Norris et al. |
| 2004/0122829 A1 | 6/2004 | Sakurai et al. |
| 2004/0155958 A1 | 8/2004 | Lee |
| 2004/0019077 A1 | 9/2004 | Pettigrew et al. |
| 2004/0190775 A1 | 9/2004 | Miller |
| 2005/0057653 A1 | 3/2005 | Maruya |
| 2005/0105770 A1 | 5/2005 | Sumitomo et al. |
| 2005/0207622 A1* | 9/2005 | Haupt .............. G06K 9/00288 382/118 |
| 2005/0212911 A1* | 9/2005 | Marvit .................. G06F 3/017 348/154 |
| 2005/0271245 A1 | 12/2005 | Ai et al. |
| 2005/0271250 A1 | 12/2005 | Vallone et al. |
| 2005/0276443 A1* | 12/2005 | Slamani ............ G06K 9/00208 382/103 |
| 2005/0280707 A1 | 12/2005 | Sablak et al. |
| 2006/0028550 A1 | 2/2006 | Palmer et al. |
| 2006/0056655 A1* | 3/2006 | Wen .................... G06F 19/3418 382/103 |
| 2006/0154642 A1 | 7/2006 | Scannell |
| 2006/0177101 A1 | 8/2006 | Kato et al. |
| 2007/0013776 A1 | 1/2007 | Venetianer et al. |
| 2007/0071323 A1 | 3/2007 | Kontsevich et al. |
| 2007/0188608 A1 | 8/2007 | Konno |
| 2007/0262574 A1* | 11/2007 | Breed ...................... B60R 1/00 280/735 |
| 2007/0263907 A1* | 11/2007 | McMakin ............ G01S 13/887 382/115 |
| 2007/0285510 A1* | 12/2007 | Lipton ............... G08B 13/1961 348/135 |
| 2007/0291115 A1 | 12/2007 | Bachelder et al. |
| 2008/0019564 A1 | 1/2008 | Murata et al. |
| 2008/0159626 A1 | 7/2008 | Ramsay et al. |
| 2009/0219411 A1 | 9/2009 | Marman et al. |
| 2009/0290023 A1 | 11/2009 | Lefort et al. |
| 2009/0297021 A1 | 12/2009 | Islam et al. |
| 2010/0141380 A1 | 6/2010 | Pishva |
| 2010/0187425 A1 | 7/2010 | Majewski et al. |
| 2011/0018769 A1 | 1/2011 | Misikangas et al. |
| 2011/0211760 A1 | 9/2011 | Boncyk et al. |
| 2012/0206337 A1 | 8/2012 | Hildreth et al. |

OTHER PUBLICATIONS

U.S. Appl. No. 12/481,483 Office Action dated Nov. 16, 2011, 18 pages.
U.S. Appl. No. 12/481,458 Office Action dated Oct. 27, 2011, 18 pages.
U.S. Appl. No. 12/481,458 Response to Office Action filed Dec. 5, 2011, 8 pages.
U.S. Appl. No. 12/481,063 Response Office Action filed Jan. 17, 2012, 11 pages.
U.S. Appl. No. 12/481,063 Office Action mailed Mar. 15, 2012, 21 pages.
U.S. Appl. No. 12/481,063 Response to Office Action filed May 30, 2012, 10 pages.
U.S. Appl. No. 12/481,483 Response to Office Action filed Feb. 27, 2012, 10 pages.
U.S. Appl. No. 12/481,458, Response to Office Action filed Jun. 1, 2012, 15 pages.
U.S. Appl. No. 12/481,458, Office Action mailed Mar. 14, 2012, 22 pages.
U.S. Appl. No. 12/481,483 Office Action mailed Jul. 6, 2012, 20 pages.
U.S. Appl. No. 12/481,483 Response to Office Action filed Oct. 9, 2012, 13 pages.
Office Action mailed Jan. 4, 2013 in related U.S. Appl. No. 12/916,283, 32 pages.
Siemens, Intrusion, Eyetec.TM. brochure, date unknown, 8 pages.
PCT/US2010/025631, International Search Report and Written Opinion mailed May 20, 2010, 14 pages.
Lucas, Y., et al. Modeling, Evaluation and Control of a Road Image Processing Chain, Jun. 28, 2005, Image Analysis, LNCS, pp. 1076-1085.
Mount, J. "Movement patterns used by the elderly when getting out of bed" (2006).
Ford-Smith, C.D. & Vansant, A.F., "Age Differences in Movement Patterns Used to Rise from a Bed in Subjects in the Third Through Fifth Decades of Age" Physical Therapy, vol. 73, No. 5, May 1993, pp. 300-309.

* cited by examiner

IMAGE PROCESSING SENSOR SYSTEMS

RELATED APPLICATIONS

This application is a continuation-in-part of U.S. patent application Ser. No. 12/916,283 filed Oct. 29, 2010 which is a continuation-in-part of each of U.S. patent application Ser. Nos. 12/481,063, 12/481,458 and 12/481,483 all filed on Jun. 9, 2009, claiming benefit or priority to U.S. Provisional Application Ser. No. 61/155,839 filed Feb. 26, 2009, and is a continuation-in-part of international application PCT/US10/25631 filed Feb. 26, 2010, the content of these applications being hereby incorporated into this application by reference.

BACKGROUND

1. Field

The present disclosure pertains to methods and apparatus for processing images. More specifically, it employs systems and software to detect and identify specific human movements or postures, which are predictors of certain activities so that interested third parties may be notified, with a preferred embodiment operating as an observation/supervision device for patients in bed who have been identified as fall risk.

2. Statement of the Problem

A variety of commercially available sensor types may be used to monitor space and report on a wide range of parameters. The sensor types are associated with different technologies, each exhibiting its own set of advantages and disadvantages. There is a need to improve sensor performance, accuracy and the ability to assess parameters of interest within the monitored space.

The most widely used sensors are of a low cost design. These sensors are crude by modern information processing standards. The currently available sensors for motion, for example, are unable to provide any information regarding detected motion and therefore, trigger for any motion that occurs in the field of view, regardless of the source of motion. By way of illustration, when a sensor is installed to turn on lights in a driveway when a car pulls up, the motion detector problematically activates for passing dogs that walk by, trees moving in a breeze, and even for an optical heat gradient created by the rising sun. These latter occurrences are all categorized as false-positive events, since the objective is selective activation for an approaching car. These sensors correctly detect an intrusion so the system is operating with sufficient selectivity to detect an intrusion event; however, specificity is poor because the system cannot discriminate to ascertain the nature of the intrusion. One solution to avoid such problems is to limit the monitored space. For example, one manufacturer of a driveway monitor device states in the product specification that the "signal should be installed at a height of 4 feet to avoid feedback interference errors from the ground." This solution is less than satisfactory because it fails to accurately detect intrusion events occurring below a certain height because of ground interference.

Current low cost sensors have poor specificity because there is insufficient resolution to discriminate between different objects or events that fall within their field of view. This inability to detect and respond appropriately for a detected object or event is directly responsible for increased cost of support and may even endangers lives. In one example, a small rodent running across the floor can set off a motion detector, triggering an intruder alarm and causing a police response. Some manufacturers offer 'pet immune' detectors, so an alarm is claimed to not trigger by the homeowner's dog for home security systems. These systems do not recognize pets. They are quantifying the heat mass of the object using an infrared sensor and, based on some threshold value, signal an alarm accordingly. Obviously, if the dog runs around the house excitedly because it hears the garbage truck outside, the heat mass will elevate possibly triggering an alarm. Furthermore, there is no ability to discriminate between a dog and a small child.

Nor is it the case that higher-end systems solve these problems in a satisfactory manner. The prior art contains a variety of programming techniques related to the processing of digital video images. Considerable prior art surrounds the processing of video images in an effort to recognize objects or events in the monitored or recorded footage. Applications are primarily intended for surveillance or security purposes. These systems use video cameras to capture video footage in the field of view and transmit the video signal, either through a cable interconnect or wirelessly, to a remote processing station where the video footage is processed. These video systems require high data bandwidth and considerable infrastructure to support the transmission of video signals to remote processing stations. These needs greatly increase the cost of deployment and operation. Also, the image analysis is performed post-event at a central processing station, which typically supports multiple video cameras. The system requirement for central processing greatly increases the required processing power of the central station, the complexity of its operation and the process is analyzing history, rather than real-time. The complexity of video systems is further increased to satisfy one of the primary purposes, which is preservation of records for future reference. Furthermore, video cameras are expensive and complex devices, which lower their reliability.

Digital imaging systems have become very inexpensive to produce. As a result, image creation is a standard feature on most modern handheld communication devices, e.g., cell phones and PDAs. Image creation technology has been commoditized to greatly reduce the cost to create a digital image. These commodity components provide a low cost, stand-alone, reliable image capture hardware platform.

Recently, systems and methods have been disclosed that have taken advantage of the commoditization of image creation technology and incorporated imaging capability into monitoring applications. U.S. Pat. No. 7,231,654, entitled "Remote Monitoring Method and Monitor Control Server" ("the '654 patent") describes method where an image capture device is added to a remote monitoring device that is connected to monitor control server. The '654 patent essentially adds an image capture capability to a conventional motion detector used for security monitoring, where an image is captured only when the motion detector triggers and the image is transmitted to the control server without any image processing being performed by the remote monitor. The control server then formats the image for transmission to a mobile terminal, such as a PDA or cell phone, where the image may be viewed by a user.

The '654 patent repeats the problems of the prior sensor art. The disclosure does not provide any imaging processing at the remote monitor and, in fact, does not provide any image processing throughout the entire system. The image capture capability is only used to capture an image and pass it through the system using various communication methods to enable the image to be reviewed remotely. The '654 patent does not provide any improvement to the sensor art and only offers improvement to the notification methods for existing security systems.

In another example of prior art that falls short of providing any improvement to the general sensor art is disclosed in U.S. Pat. No. 6,697,104 ("the '104 patent"), entitled "Video Based System and Method for Detecting and Counting Persons Traversing an Area Being Monitored." The '104 patent discloses a dedicated remote video device having a single function, namely, to count the number of people that enter or exit a monitored area. The data collected by the remote monitoring device must be uploaded to a remote processing station where additional processing activity is required to provide any useful value. Several prerequisites exist regarding the deployment environment that severely limits the functional value of the disclosure. The '104 patent provides some limited ability to 'configure' the remote monitoring device once it is installed at its deployment location to account for the environment of use however, the configuration capability is limited to the 'area of interest,' subdividing the field of view. Accordingly, the 'counting' function is limited to only a part of the captured video signal.

Using video signals, the remote monitoring device of the '104 patent processes frames of video but never actually recognizes the presence of a person. There is merely recognition of artifacts of "what might be a person." For example, if a dog were to pass through the field of view, the system may or may not count the dog as person. This happens because the '104 patent relies upon on a static background image. There is subtraction of this background to identify a patterned characteristic change in the background that is assumed to represent a person; however, this is not a process that recognizes the object itself. Only an artifact of the image is observed as a change in the background. Furthermore, the '104 patent registers person counts in some internal counters that must be uploaded to another computer system where the counts must be processed and formulated into a useable format for a subscription based customer model. The remote monitoring device does not produce output that contains any actionable information. The single, dedicated function of the remote monitoring device cannot be reprogrammed, and its inability to receive 'count' objects other than people is limiting.

U.S. Pat. No. 7,190,259 ("the '259 patent") discloses a lens arrangement to create a 360 degree view for a video imaging component. The system displays the captured image on a screen. The lens is deployed in the exterior rearview mirrors of an automobile. The image is displayed for driver viewing. The omni-directional vision sensor merely delivers output for presentation of the image and does not process the image.

U.S. Pat. No. 7,414,647 ("the '647 patent") describes another lens arrangement to create a 360 degree view for a video imaging component. Again the system displays the image on a remote terminal screen. The image capture and processing device has limited processing to format the image data into either panoramic or perspective views for display purposes. A mobile body detecting section is disclosed for detecting a moving body in the field of view. The primary application disclosed is for deployment in an ATM to capture images of ATM users. A 'communication section' telecommunicates with an external terminal device. The data can be transmitted either wirelessly or via cable interconnect but again, its limited strictly to image data. There is no discussion anywhere in the disclosure of the image capture and processing device receiving any information or of the communication section being used to receive data.

U.S. Pat. No. 7,200,246 ("the '246 patent") discloses an imaging system and method directed toward industrial equipment safety by monitoring an 'area of interest' and detecting an object entering the area. The image capture and processing device contains image processing algorithms for object detection, an output signal and the ability to connect a PC to the image capture and processing device for configuration. However, the disclosed capability all relates to an 'area of interest' in the manner of a motion detector and do not address the selective identification of 'objects of interest', nor are any image processing functions or algorithms transferred to image capture and processing device through the PC connection.

The 'area of interest' is monitored by the image capture and processing device employing a defined border area. The image processing relies on the use of a reference image, where sampled images are subtracted from the reference image and changes in pixel pigmentation are used to determine if an object has 'breached' the border of the monitored area of interest. While the disclosure includes discussion of establishing a 'threshold' for the number of pixels required to trigger an output signal, even referencing a "hand", there is no attempt by the '246 patent disclosure to recognize the object breaching the border.

Human falls are the leading cause of injury for persons over the age of 65 and can occur in any environment, including hospitals, long term care, retirement housing or single family dwellings. Falls are especially prevalent in health care environments where patients under care generally have reduced physical or mental capacity. The occurrence of falls in health care environment is so pronounced that the reduction of the number of injuries resulting from patient falls is one of the Joint Commission's patient safety goals. The growth in the number of older adults has led to more aggressive efforts to promote independent living and expansion in monitoring the well being of older individuals, for all possible living environments. Given the occurrence of falls, the need to monitor and report has become a critical element of society. While falls can occur during any activity, the great percentage of incidences occurs when an individual transitions from lying down or sitting.

Monitoring human activity is not limited to fall risk individuals. General monitoring of elderly who live alone is a prime activity monitoring application. Many other applications exist, for example, with prison and jail overcrowding, the image capture and processing system can be trained to look for particular movements or postures, which are characteristic of activities that may be harmful to prison personnel or inmates, specifically inmates who are placed on suicide watch. Other example applications include schools, which have become increasingly hazardous and the present instrumentality can be used to monitor children leaving designated areas or other individuals entering certain school areas and identifying suspicious articles being carried. Other applications will become apparent to those skilled in the art and this disclosure will focus on a generalized description of a bed monitor application.

There are a number of different patient bed monitoring systems and methods disclosed in the prior art. Most of the bed monitoring systems disclosed involves some contact with the patient. Patient contact requires the sensor component of the patient bed monitor system to be properly positioned or attached to the patient, which makes it subject to mis-alignment or removal by the patient that generally results in a false alarm. Another considerable drawback of system and methods described in prior art is that they are limited to reporting on the presence or absence of patient, as described in U.S. Pat. No. 6,917,293 to Beggs (Beggs '293). Reporting the absence of a patient from bed is too late as the patient is already out of bed unassisted with a 30% chance he or she has already fallen.

One disclosed bed monitoring system utilizes image analysis and purports to provide utility for fall prevention and detection. The system described in U.S. Pat. No. 5,541,934 to Fredriksson (the '934 patent), as with other devices, is primarily used for reporting that a fall has occurred. Further, the disclosed invention relies on an optical sensor given in a separate patent, where a central station is claimed for receiving images to be reviewed by an operator. Another drawback of the '934 patent is that it requires images to be saved for later analysis if some future event occurs. This specifically teaches away from a real-time image analysis system. Saving images and transmitting to a remote location raises privacy concerns for patient monitoring and makes the '934 patent unsuitable for use by health care facilities.

The '934 patent includes language whereby the invention purports to provide fall prevention by identifying a person leaving the bed to end up standing beside the bed. The need for the invention to have a person go from laying down to standing beside it in order to recognize the motion before issuing an alarm renders the invention commercially unsuitable for fall prevention. Once the person is standing, the invention provides nothing to prevent the individual from falling and any alarm is too late. This also holds true for an alarm if a person sitting on the edge of the bed as it results in reduced reaction time for a care giver to arrive before the person is standing. The fundamental drawback of the '934 patent is that the methods described with the various algorithms are only able to detect that a change has occurred between the current image and previous images. The '934 patent classifies all changes between images as motion and then attempts to measure the change at defined states (standing, lying on the floor, etc.). The limitations imposed by the '934 patent are due to the fact that the system uses "blobs", which is a term of art in the computer science field and can be generally regarded as a collection of binary data. Blobs do not provide any internal information and can only be characterized by their size and, if an edge detection algorithm is properly applied, information regarding their shape. In the case of the '934 patent, the disclosed invention makes use of the orientation, or aspect ratio of blobs to trigger alarm conditions without any knowledge of what the blob represents. Again, the '934 patent teaches away from real-time image processing and issuing an alarm by incorporating a delay period needed to confirm the orientation of the blob. The '934 patent does not contemplate any attempts to classify the 'type' of motion. It is necessary to detect and identify specific type of motion or postures in order to provide a reliable predictor, or notification, that a person is about to get out of bed.

All disclosed patient monitoring prior art incorporates the requirement to delay issuing an alarm to reduce the incidence of false alarm.

The need exists for an improved system and method that provides care takers with a reliable, advanced warning or notification that a patient is about to get out of bed without assistance and that does so without delay and a very low incidence of false alarms.

SUMMARY

The present instrumentalities overcomes the problems outlined above by providing a non-contact monitor that can detect and classify types of movements or postures associated with an individual getting out of bed, providing attendants with an advanced notification or alarm to react and thereby minimizing the likelihood of an unassisted bed exit that leads to injury.

DETAILED DESCRIPTION

Figure 1:
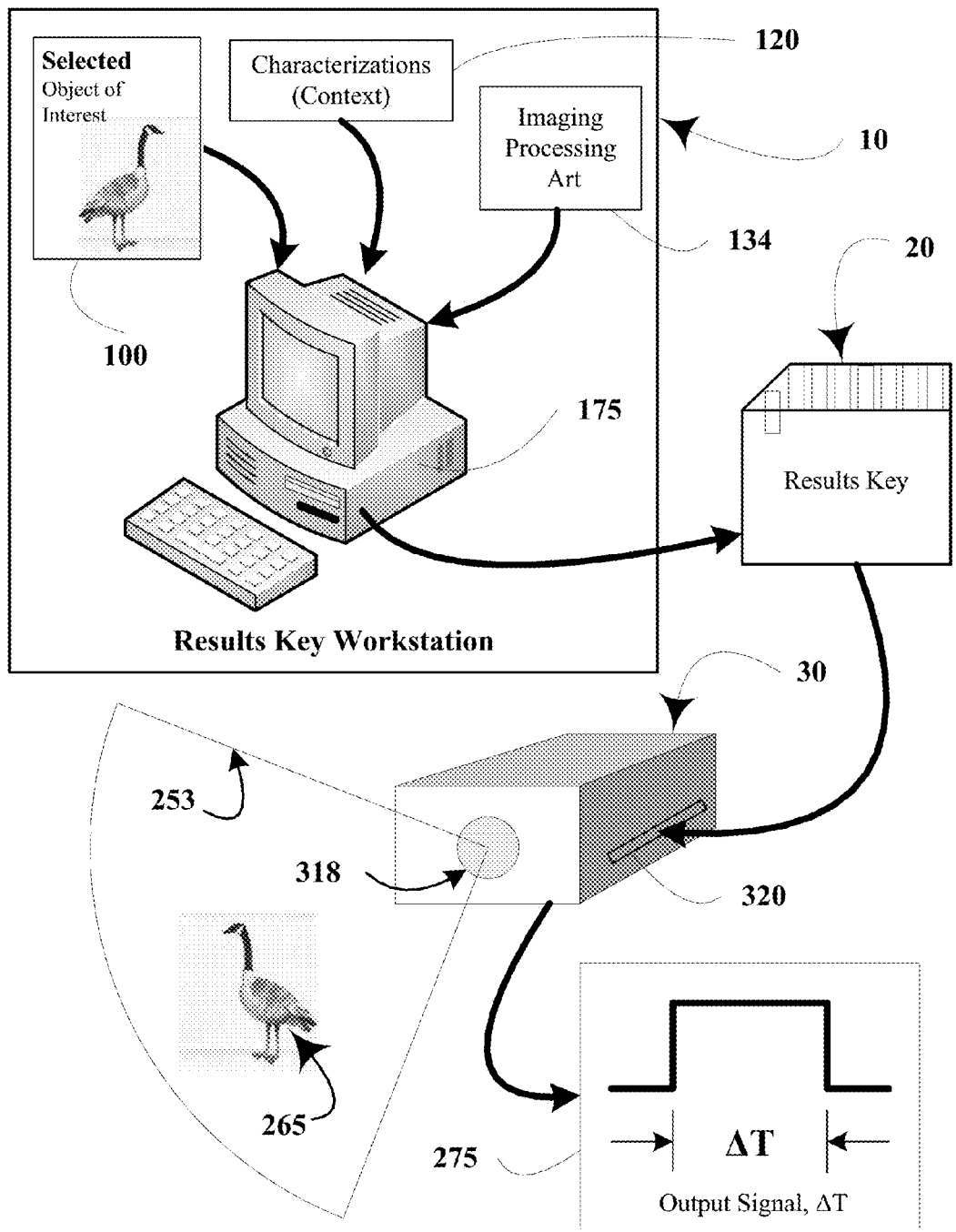
FIG. 1 is a system level diagram according to the present system.

FIG. 1 provides a system level representation of the present system, depicting the major components according to one embodiment. The major components include a Results Key workstation 10, Results Key 20 and an image capture and processing device 30. Results Key workstation 10 may be programmable circuitry, such as a standard personal computer with sufficient processing capability to manage, manipulate and process digital images of any available resolution and includes standard components and peripherals as is customary for such information processing tasks. Program functions of the Results Key workstation 10 include storage of image representations for selected objects of interest 100, characterization 120 of the object of interest and image processing art or instructions 134, all of which are collectively used to construct, formulate or otherwise create a Results Key 20 for the selected object of interest 100.

Selected objects of interest 100 may include any identifiable object or event that is living, inanimate or observed and is desired to be the subject of analysis for the purpose of recognition. One of the more popular selected objects of interest 100 is a human being in its various shapes, sizes and groupings. Other living objects include such creatures as pigeons, geese, bear and deer; animals that have proven to be a source of nuisance for inhabited areas. Inanimate selected objects of interest 100 are as varied as there are objects found in the physical environment, including any manufactured product and all their individual parts. Selected objects of interest 100 also incorporate contextual image artifacts as well, and include, but is not limited to, such artifacts as background and ambient lighting conditions.

Characterizations of the selected object of interest 120 consist of programmable predetermined or defined generalizations about the object of interest 100 that may be used or applied as rules to extract features about the selected object of interest 100. The generalizations can be positive or negative characteristics, i.e., they may define what is of interest and what in NOT of interest. The generalizations may be true, false or conditional, under any Boolean state of logic. These programmable logic statements may describe anything that exhibits a consistent characteristic of the selected object of interest 100, with or without regard to scale.

The image processing instructions 134 may originate from known sources, such as imaging processing algorithms from the public and private domain, together with custom functions and algorithms developed as original works of authorship or modifications to existing software according to the instrumentalities described herein. In one aspect, the image processing instructions 134 may be provided as proprietary or open source implementations of algorithms from the public/private domain.

The Results Key workstation 10 is used to construct, formulate or otherwise create Results Keys 20 for the selected objects of interest 100, 265 as related by the Results Key 20. Results Key workstation 10 also manages completed Results Keys 20 in a manner that is similar to practices used for software configuration management and revision control methodologies well known within the software industry and to those skilled in the art. Results Key workstation 10 also provides modeling of the image capture and processing device 30 to simulate operation of the Results Key 20 prior to its release and deployment to the field.

Results Key 20 provides for the transfer of image analysis and processing know-how from one hardware platform, i.e., the results key workstation 10, to the image processing and capture device 30. Once configured for operation by incorporating one or more of the Results Keys 20, the image processing and capture device 30 operates as a separate and/or remote hardware platform on a standalone basis that processes sample images and recognizes the presence of the selected object of interest 100 within the field of view 253. While the preferred embodiment depicts the use of a standard SD memory card 320, those skilled in the art understand that there are a wide variety of methods available to facilitate the transfer of software and computer code from one hardware platform to remote hardware platforms and many of these alternate methods are disclosed below.

Making the Results Key 20 available to the image capture and processing device 30 programmably configures the image capture and processing device 30 for a specific application or implementation. In one aspect, the present system may provide a standalone hardware platform that may be selectively reprogrammed by the provision of different Results Keys 20 to satisfy a wide variety of desired applications. Prior sensor hardware has historically been single purpose, limiting their application to the measurement or detection of individual physical properties. Sensor prior art has been centered on the measurement or detection of an artifact of an object of interest resulting in a large percentage of false-positive or false-negative results. The present system overcomes these deficiencies by detecting, measuring or recognizing the detected object of interest 265, providing a substantial improvement over the sensor prior art.

With the Results Key 20 available to the image capture and processing device 30 through SD memory card 320, sample images are captured from the field of view 253 (shown in FIG. 1). Lens 318 defines the imaging boundary for the field of view 253, which may range from tenths of a degree to 360 degrees. In one embodiment, a wide angle lens or fisheye lens is electronically or mechanically configured to provide input from a limited field of view that is less than the total field of view. Thus, a single lens may become, in effect, a beam detector for one or more beams each having no requirement for a discrete or separate beam source. Different lens arrangements are contemplated to minimize distortion of sampled images however; an improvement disclosed by the present system is the incorporation of image distortion in the Results Key 20 to minimize the need to eliminate image distortion. Captured images from the field of view 253 are processed by the image capture and processing device 30 in cooperation with Results Key 20. If the processed image contains a detected object of interest 265, the image capture and processing device 30 activates output signal 275, which remains active for a time, $\Delta T$, as defined by information contained in the Results Key 20.

The method and apparatus of the present system has nearly limitless applications and output signal 275 may be used to drive or initiate secondary processes, systems, methods or apparatus that are appropriate for the particular application. For example, if used for security or intrusion detection, output signal 275 is electrically or wirelessly supplied to a remote alarm notification system, as the present system is a drop in replacement for motion or heat detection sensors presently used by the security industry for greatly improved performance. Another example is where the present system is used for patient observation and output signal 275 is used to trigger an alarm at the nurse call station. Yet another example is when used for manufacturing process monitoring, output signal 275 is supplied to a mechanism to open a diversion path to out-sort assembly line packages with missing labels, for example. The foregoing examples are illustrative only with many other implementations possible for the use of output signal 275 as will be recognized by one skilled in the art.

Figure 2:
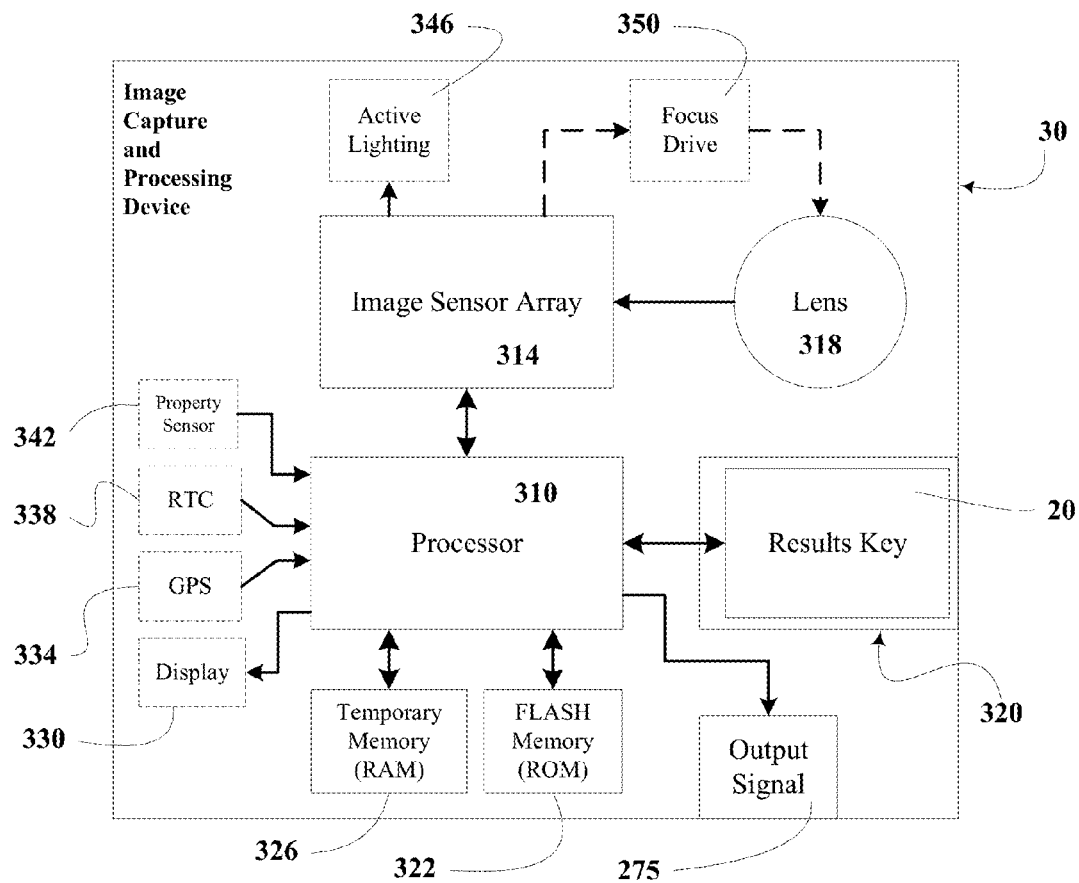
FIG. 2 is a detailed drawing of an example embodiment of the image capture and processing device.

FIG. 2 provides a detailed schematic representation of the image capture and processing device 30, which is also referred to as the image-based recognition sensor and the drawing includes both required and optional components. In one aspect, the present system may provide a low-cost, programmably configurable sensor platform for use in a nearly infinite number of applications. One of the principally useful technologies for the present system is the commoditization of the image capture component shown in FIG. 2 as the image sensor array 314 and lens 318. Recent advances in technology and manufacturing processes have allowed these two functional elements to be combined in a single integrated circuit, driving down the cost of manufacturing and increasing the reliability of the image capture function. This technology has allowed image capture features to proliferate, such that the ability to capture a digital image is common place and a feature of most modern, handheld communication devices. The present system utilizes this low cost, high resolution technology by incorporating this integrated circuit in the image capture and processing device 30. Accordingly, the image sensor array 314 may provide commercially available image capture and conditioning functions, such that the output of sensor array 314 is a complete digital image supplied in any number of standard digital image formats. Resident functions that are a part of the image sensor array 314 include a signal for active lighting 346 and a focus drive 350. Diagramed elements 346 and 350 of FIG. 2 are shown as optional components for the image capture and processing device and are disclosed below as an alternative embodiment.

Processor 310 controls the image sensor array 314 and manages the processing function applied to the sample digital images created by 314. Minimum requirements for the preferred embodiment include memory and a circuitry to issue output signal 275. Memory blocks 20, 322 and 326 shown in FIG. 2 are conceptual and shown for illustrative purposes only and are not intended to convey physical components. Temporary memory 326, often referred to as Random Access Memory (RAM), is used for data storage as part of the device 30 operation and image processing functions. The FLASH memory 322, often referred to as Read Only Memory (ROM), is used for storage of code that typically includes the operating system and other supporting software functions that are common to all applications or deployments of device 30. The Results Key 20 shown in the representative diagram of FIG. 2 as an SD memory card, which is a type of FLASH memory used to store computer code and is this representation, it stores the computer code that represents the Results Key 20.

These components are shown by way of nonlimiting example and may be selectively reconfigured as a matter of design choice. As depicted, the image capture and processing device 30 has memory with these three types, all of which can be performed by various combinations of physical components given the advances in the electronic memory art and the availability of a variety of memory components and technologies. An alternate embodiment is for the image capture and processing device 30 to operate out of a single physical ROM memory 322 component and as an example, Results Key 20 can serve to store the Results Key and the operating system as will be recognized by one skilled in the art. The inverse alternate embodiment is also disclosed where the Results Key 20 is stored in FLASH memory 322, where the Results Key 20 is transferred to the image capture and processing device 30 via wireless transmission, which results in no memory card being required.

Output signal 275 includes any means that is commonly used to communicate signals or information, including wired interconnect or wireless transmission using any frequency in the electromagnetic spectrum, which also include e-mails or text messages as is becoming a common practice in the information technology industry.

Also shown in FIG. 2 are optional components 330, 334, 338 and 342 that may be incorporated into the image capture and processing device 30. An optional display 330 provides status information and other operational notification messages and is suitable for certain applications. The preferred embodiment for this optional component is an inexpensive, one line Liquid Crystal Display (LCD) that produces static and scrolling message output. A Global Positioning System (GPS) function provides positional information that is used in conjunction with information provided by the Results Key 20 to further enhance the capability of the image capture and processing device 30 to recognized detected objects of interest 265 that possess positional characterizations 120. Based on the deployment of a generic image capture and processing device 30, the likelihood or probability of a detected object of interest 265 can vary by latitude and longitude, which is accounted for in the Results Key 20 based on characterizations 120.

Like positional information, time is also a useful parameter to enhance the performance of the image capture and processing device 30 and is supported by the optional Real Time Clock (RTC) 338. By maintaining the time of day, the image capture and processing device 30 can be directed by the Results Key 20 to limit activation of output signal 275 to only certain blocks of time or be provided information concerning the time of day where the detected object of interest 265 is more likely to be present.

Yet another optional component that enhances the performance and accuracy of the image capture and processing device 30 is the integration of traditional physical property sensors 342 for motion, heat, sound, etc. As will be recognized by one skilled in the art, the integration of one or more of these property sensors 342 to support the recognition of a detected object of interest 265 will greatly increase the measures of confidence for a suspected detection. As will be further recognized by one skilled in the art, other optional components exist that support enhancement of the image capture and processing device 30 and the foregoing disclosure is not intended to limit the means or methods used to increase the accuracy, reliability or performance of the present system.

Figure 3:
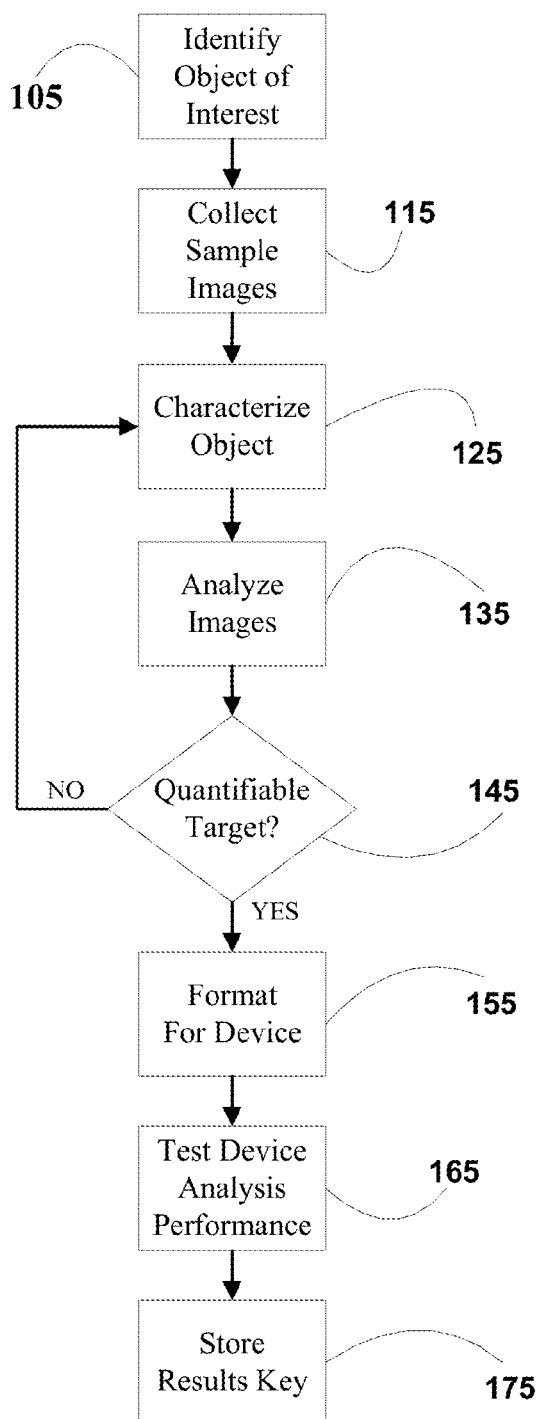
FIG. 3 is a schematic block diagram of an example embodiment for constructing an image analysis data set or Results Key.

FIG. 3 depicts an overview of the process to construct an analysis data set or Results Key 20. The first step in the process is to identify 105 the objects of interest 100 (See FIG. 1). The object of interest 100 may be any identifiable object or event that is living, inanimate or observed and is desired to be the subject of analysis for the purpose of recognition. One of the more popular objects of interest 100 are human beings in various shapes, sizes and groupings. Other living objects include such creatures as pigeons, geese, bear and deer; animals that have proven to be a source of nuisance for inhabited areas. Inanimate objects are as varied as there are objects found in the physical environment, including any manufactured products and all their individual parts.

Objects of interest 100 are not limited to particular elements that can be identified by the existence of a boundary or closed shape. Objects of interest also include observable aspects of the physical environment, or events, and include such aspects as color, motion or interaction between objects, for example. A "color" event can be as simple as the change in ambient light as the sun sets, going from daylight to evening to nighttime or, more complex events, such as the color consistency of two fluids mixed together.

Once an object of interest has been identified 105, sample images are collected 115. Sample images can come from a variety of sources including actual images of objects that are captured using a remote device, such as a digital camera, camcorder or the apparatus of the present system. Sample images can also be computer generated graphics using widely available computer graphics software that has advanced to a capability that provides extremely realistic representations of objects. Use of computer generated graphics allows cost effective management of creating a varied range of samples for the object of interest 100 to represent the variations typically found in the physical environment. Physical models of the object of interest can also be used and even images of pictures of the object of interest 100 satisfy the need for sample images in the collecting step 115. In the simplest form, a line drawing or stick figure may also be used for object samples. The number of samples depicting variation of the object of interest 100 as well as the complexity of the samples (actual humans' verses stick figures) has an impact on the quality and complexity of the analysis. The quantity of sample image required for the construction or creation of Results Keys 20 may range from zero (0), to extensive video footage that is sectioned out frame by frame. In one embodiment, the image capture and processing device 30 is installed at its desired deployment location and sample images are collected, stored and retrieved from the device and used in the collecting step 115.

As shown in FIG. 3, step 115 collects sample images in a sequential order of process steps, however; the collection process may be ongoing throughout the entire effort of constructing the Results Key 20. Thus, the collecting step 115 may be performed at any time, adding additional images to the sample set on demand. Other process steps may determine additional samples are required, including samples that highlight variation in the representation of the object of interest.

Once the collecting step 115 provides a sufficient number of sample images to represent the variations of the object of interest 100, the object is characterized 125. Generalizations about the selected object of interest 100 are defined and used to extract features and formulate rules about the object. The generalizations may be positive or negative characteristics to define what is of interest and what in NOT of interest, and may be true, false or conditional, under any fundamental condition of Boolean or computer logic used in computer programming. These descriptive logic statements are used to describe anything that exhibits a consistent characteristic of the object of interest 100. An example of a simple generalization includes; the object contains only obtuse angles or conversely, the object contains no obtuse angles. Other geometric descriptors can be utilized, as well as color, size, clustering and type of motion and frequency of appearance.

In one example, a motion characteristic specifies that the detected object of interest 265 must progress through the field of view at a speed of 5 feet per second plus or minus 2.5 feet per second or, and the object of interest 265 will always move from left to right across the field of view. Generalizations to characterize the object of interest 265 can also use fundamental logic functions such as "and" and "or" statements to form conditional generalizations. For example, the object has one obtuse angle 'and' some portion has a curvilinear boundary. Characterizing the object of interest can also include partitioning the object and crafting generalizations with respect to each portion and then a top level generalization that relates the partitions to one another.

Characterizing the object of interest 100 may also include generalizations about the intended application when deployed in the image capture and processing device 30 in the field. Results Key 20 can also contain information about the deployment, whether it is indoors, outdoors, hot or cold climate, latitude/longitude, etc. Information concerning the arrangement of the lens 318 and image sensor array 314 to be employed by the image capture and processing device 30 for the particular application are also specified through characterizations. Wide angle lens, filtering or the need for digital/mechanical zoom are examples of, and not limited to, these types of characterizations. Further, certain applications may have different accuracy requirements that are driven by the consequences of the false-positive or false-negative results. A grading scale for the intended application can be used, similar to that used for the failure classification of medical devices, where Class 1 is non-critical and will not endanger life, Class 2 is where a failure may contribute to a life threatening situation or Class 3 is for device failures that creates a life threatening situation. Using a similar scale to characterize the intended application for the object of interest 265 will assist in establishing a necessary level of analysis in the following process step.

Components of the characterizations are features and discriminators for the object of interest 100. Features are individual structure, form or appearance of a prominent part or property of the object of interest 100 that can be the subject of analysis and result in a high probability of repeatable recognition. An object of interest 100 may be spatially partitioned, sectioned or separated into many different features and the recognition of one or more can be sufficient to recognize the entire object with acceptable confidence. A discriminator, in the context of the present system, is essentially an "anti-feature", where the presents of a discriminator provides a negative contribution toward the desired level of confidence level that the object of interest 265 is present. The use of these two concepts has ability to make the process of recognizing the object of interest 265 extremely efficient.

There many other possible characterization categories or parameters that will be obvious to one skilled in the art and foregoing disclosure are for illustrative purposes only. The characterizations in step 125 establish a framework for step 135, where the object of interest 100 is analyzed.

Analysis 135 of the sample images from step 115 is a process where images are examined and processing techniques are selected to reduce the object of interest 100 to computer logic to form Results Key 20. The data or information contained in Results Key 20 ranges from flat file passive information used by the software/firmware resident within the image capture and processing device 30, to discrete executable software module(s) that are launched by the image capture and processing device 30 operating system. In one aspect, the Results Key 20 may contain a combination of flat file information used to 'configure' the image capture and processing device 30 and executable software modules used to analyze sample images, which consists of, but is not limited to, processes, know-how, designs, formulas, developmental or experimental work, improvements, discoveries, computer programs, original works of authorship and hardware configuration. Results Keys 20 are considered intellectual property that are either patentable or eligible for copyright protection.

Analyzing 135 involves computer processing of the sample images to a sufficient level to be able to identify the object of interest 100 within the sample image with some statistical level of certainty. The characterizations developed in step 125 establish an appropriate level of statistical certainty if the range of variability of the object of interest 100 makes the computational requirements unreasonable or unattainable. For example, if the object of interest is a specific component in an assembly process, located in an identical position with identical orientation and lighting, it is likely that the component can be identified with near certainty (99.95% for example). On the other hand, if the object of interest 100/265 (See FIG. 1) is a goose, it may be that a 60% certainty is adequate as the Results Key 20 cannot distinguish between a goose and chicken but this deficiency is irrelevant for the intended application. Likewise, if the application is to identify a human being (the object of interest 265) in the driveway of a home to turn on a convenience light and the object of interest 265 can only be identified with a 30% certainty, the fact that something is in the driveway may be sufficient to supply an output signal 275 from the image capture and processing device 30 (to turn on the light). This latter case is an example of a non-critical application and the present system provides an improvement over the existing art as the output signal 275 from the device is not supplied for a tree moving in the breeze, for example.

The central functionality executed in 130 is processing the sample images 110 using image processing software algorithms 134. There is a considerable volume of knowledge in the public domain surrounding imaging processing algorithms 134 and one of the more comprehensive publicly available collections is titled Open Source Computer Vision Library, or OpenCV. OpenCV is a library of programming functions mainly aimed at real time computer vision and includes a comprehensive set of operational computer code modules that supports a wide range image processing and image manipulation techniques. The functions maintained by the OpenCV resource are available for use and incorporation into third party products as an open source project will continue to evolve and improve under the open source development model. This resource, and others like it, will continue to advance the image processing art 134 in the public domain. The present system incorporates the availability of this information and its improvements.

The present system makes use of the availability of the image processing techniques 134 in the public domain by including an operating platform that provides a means to execute the various functions individually or in combination. Image processing techniques and functions 134 include, but are not limited, operations performed on digital images, such as; convolution, derivatives, transforms, coordinate conversions, filters, segmentation, background subtraction, etc. It is expected that each individual object of interest 100/265 to be recognized in its resident environment will warrant a unique set and structure of image processing techniques and functions 134, tailored to the specific application.

Commonalities between different Results Keys 20 may evolve as the number of objects of interest 100 addressed grows and experience is gained with different environmental backgrounds. The range of analysis can vary for the given particular deployment application from a very simple, single function or algorithm to complex serial/parallel multi-function or algorithm chain of processing. The body of knowledge developed to support the creation of Results Keys 20 include generic or "stock" functions or algorithms that have simple, standard inputs and outputs that are based on standard formats of digital images that are be applied automatically to sample images without intervention. Other functions or algorithms contain parameter settings that require some amount specification prior to their execution on sample images. A third category of functions or algorithms may require original development or code modification to existing functions and algorithms to provide utility for the instant Results Key 20 construction. As a result, construction of Results Key 20 can be completely automatic or require a software development effort. For example, a deployment application may require only the detection or recognition of any change in the field of view 253 and a simple, generic background subtraction function may suffice. On the other hand, if a deployment application requires a conditional outcome, software may need to be developed to link the outcome of the first condition to the second, for example. Further, different image processing techniques and functions may be used for objects of interest, backgrounds and deployment environments. For example, there are distinct differences between field of view 253 backgrounds such outdoor landscaping, an interior office space or the busy street corner of a large city. This improvement to the knowledge base over time will continue to benefit deployed image capture and processing devices 30 by upgrading Results Keys 20 as advances in recognition capabilities are realized.

Utilizing the characterizations developed for the object of interest 100 established in step 125, a function or set of functions are selected to process the sample images that are appropriate to create knowledge, or intelligence, regarding the object of interest 100. Additional functions are applied to the sample images until sufficient knowledge or intelligence about the object of interest is gained in order to provide a quantifiable target, as identified in step 145. This may be an iterative process that requires review or revision of the characterization 125 of the object of interest 100, the addition or tuning of function(s) in the analysis step 135 and review of the outcomes until a quantifiable state 145 is achieved.

The image processing functions 134 can be employed in a serial or parallel manner to achieve the level of necessary quantification 145 of the object of interest 100. A serial approach is characterized by the output of one image processing algorithm being used as an input for another image processing function. In this instance, the first image processing function modifies, alters or converts the sample image into a format or representation necessary for the second image processing function. An example of this is that a second imaging processing function may require an image be in a grey-scale format and the first image processing algorithm converts the color sample image to grey-scale. Other image analysis techniques for a given object of interest may be suitable for parallel application of image processing functions. In this case, two or more image processing functions operate independently of each other and generate their respective analysis outcomes. These outcomes are then operated on externally from the prior image processing functions to generate a separate outcome. As will be recognized by one skilled in the art, there are a variety of processing pathways possible given the selected object of interest, the environment in which it will be detected within and the level of confidence required for the particular application.

The preferred approach for the present system is for construction of the Results Keys 20 to be performed on a standard personal computer 10 with sufficient processing power to manipulate and manage digital images and graphics and supports the necessary interfaces and software tools. The present system contemplates a custom software application that automates the management of image processing functions 134 and has the ability to report outcomes of the analysis step 135. Other systems are suitable for the aforementioned processing and information management functions as will be recognized by one skilled in the art.

Quantification 145 of the object of interest 100 can be represented by various parameters related to the object of interest 100. Quantification 150 is subject to the results of the analysis in step 135 and consists of the output of the functions and algorithms used to process the sample images in step 115. Depending on the type of function or algorithm used, the result of the analysis can take many different forms, including, but not limited to, character vectors, matrices or arrays of numerical values, intensity values, spot specific information, specification of detected edges and/or corners, contours, histograms, etc. Quantification 145 generally involves a "threshold" for one or more measurements that are calculated for a particular image. For example, a histogram will establish a set of measures for an image and quantification 140 requires that all or some subset of values in the histogram exceeds a defined set of threshold values. Other instances involve a mathematically calculated distance between the centroids of two features within an object of interest. Thresholds can also be geometric features where, for example, if the object of interest is a beach ball, one of the pieces of information used to achieve a quantifiable state is the expression "angles<1". As will be recognized by one skilled in the art, quantification can take a variety of forms, all of which are incorporated by reference herein. Quantification 145 may be achieved directly from the information provided by one or more functions or algorithm or, the output of two or more functions or algorithms can be combined in some manner to quantify the object of interest. There are instances of functions or algorithmic combinations that form decision trees and based on the outcome of the present computation, alternate computational paths are traversed based on the decision parameters. The end result of step 145 can be to identify, classify or otherwise recognize the object of interest 100 with a level of statistical confidence.

It should be noted that there are many approaches possible to accomplish steps 115 through 145 inclusive, which reduces to the capability to process an image and identify, classify or otherwise recognize features or objects within the image. The disclosed process steps 115 through 145 has been identified in prior art and is sometimes referred to as the Image Processing Chain (IPC), as in a paper presented at Image Analysis; 14$^{th}$ Scandinavian Conference; SCIA 2005, titled "Modeling, Evaluating and Control of a Road Image Processing Chain". The capability presented in this paper differs from the present system in that it discloses a system whose intent is to identify an obstacle, rather than a specific object as disclosed herein. Further, the image capture and processing device 30 is not provided any information regarding the detection, identification, classification or recognition of the obstacle developed by a remote system, such as Results Key workstation 10.

The capability to quantify an object of interest or conducting an Image Processing Chain (IPC) can be derived from the use of individual, publicly available functions and algorithms that are properly sequenced and/or linked or, by using one or more commercially available software products that provide some or all of this required capability. For example, Intopii produces a product called NEMMA® and is marketed as a "learning image analyzer" and is targeted at texture analysis. Another product, called MATLAB® Imaging Processing from a company named The MathWorks located in Natick, Mass., markets a software package that provides many of the functions necessary to perform 130 but additional software code is required to support steps 115 through 145.

The flexibility afforded by the present system to accomplish steps 115 through 145 is, in fact, an object of the present system. The present system anticipates advances and improvements in the image processing art and incorporates by reference such advances and improvements. The present system establishes a platform for the advance of the image processing art 134 by claiming an interface between the processing functions given in FIG. 3, specifically steps 115 through 145 and the run time process as described below and shown in FIG. 4. The advances and improvements in the image processing art 134 can come from either the public domain or from third party products that can be used to support the present system through licensing agreements. An object of the present system allows the system to remain at the forefront of the image processing art 134.

Once the object of interest 100 has attained a quantifiable state 145, the Results Key 20 is formatted for the image capture and processing device 30 in step 155. The Results Key 20 consists of a variety of computer code that must be configured to operate with the hardware and software environment of the image capture and processing device 30. The hardware and software environment of the image capture and processing device 30 is supported by an operating system (OS) suitable for managing hardware and software systems. One such OS is a Real-Time Operating System (RTOS) called VxWorks and marketed by Wind River, headquartered in Alameda, Calif. Formatting of the Results Key 20 typically involves compiling the analysis data set produced by steps 135 and 145 for interaction with the image capture and processing device OS. The outcome of compiling the analysis data set is typically a computer code "module" that interacts with the OS through function "calls" that passes data and instructions between the two blocks of computer code or, the OS can be integrated with the Results Key 20 such that the outcome of the compiling is a single software module. Variations from these two possible approaches exist as will be obvious to one skilled in the art and such variations are incorporated by reference herein. Regardless of the method used in step 155, the output of this process is a "load module", which is the input for step 165.

Typically, the operating platform of the Results Key workstation 10 that is used for constructing the Results Key 20 will not be the same as the operating platform of the image capture and processing device 30. The intent of the foregoing steps is to closely model the operating platform of the image capture and processing device 30 however, discrepancies in the modeling may need to be acknowledged and accounted for between the two platforms. Format for device 165 is also used to optimize the Results Key 20 code set to minimize the amount of memory required for the Results Key when operating with the image capture and processing device 30 and at the same time maximize the efficiency. Step 165 is used to verify the load module and test it using the operating platform of the image capture and processing device 30 while in proximity of the Results Key workstation 10. This allows for changes to be easily made in the load module should any discrepancies in modeling exist. Step 165 is also to confirm the characterization of the object of interest 120, which can include response time requirements and levels of confidence required for an intended application.

The final step in FIG. 3 is to store 175 the Results Key 20 for distribution to image capture and processing devices 30 as required, maintain the Results Key 20 for future reference and inclusion in a library of objects of interest 100. The information stored at the completion of the process shown in FIG. 3 includes all artifacts generated from each process step to fully document the construction of a Results Key 20 for an object of interest 100. This allows the process for a particular object of interest 100 to be reconstructed if necessary and to build a knowledge base for the future construction of Results Keys 20 for new and different objects of interest 100. Further, as the image processing art advances and improves, an existing Results Key 20 can be updated with any applicable techniques that will enhance its performance or detection confidence level.

With Results Keys 20 constructed and stored, they are available for use by one or more image capture and processing devices 30. A representative deployment and operation process flow chart is given in FIG. 4 that begins with installing the image capture and processing device 30 in the desired location. There are many factors that can be considered regarding the installation site that principally revolve around the field of view and environmental considerations. Installation of the device requires an assessment of the field of view 253 and should take into consideration the desired monitoring area. The image capture and processing device 30 has improved range capability over other types of sensors in that the present system possesses a non-mechanical digital zoom feature to increase the volume of the field of view 253. This extended range is further enhanced by the use of available lenses 318 that provide a wide angle view to cover up to 180 degrees in the x, y and z directions. Additional embodiments of the image capture and processing device 30 includes 360 degree coverage of the field of view 253 when mounted above, below or on a vertical surface relative to the field of view for both indoor and outdoor applications. The field of view 253 can also be effectively reduced to tenths of degrees through lenses 318 and image segmentation embedded in the Results Key 20. The present system contemplates mechanical zoom and focus methods common to cameras and camcorders, but this is less desirable given the complexities introduced by such a feature. The same holds true for image capture and processing devices that are mounted using gimbals or actuators. While these mounting methods are contemplated, the preferred embodiment as disclosed above provides essentially the same capability but with lower complexity. The desired field of view 253 is incorporated in the characterization of the object of interest 120 when the Results Key 20 is constructed. As will be obvious to one skilled in the art, the present system discloses a universal field of view 253 given the possible combinations of mounting location, incorporated lens 318 arrangement in the image capture and processing device 30, digital and mechanical zoom, multiple imaging components per device 314/318 and the characterization 120 of the field of view 253 during the construction of the Results Key 20.

Figure 4:
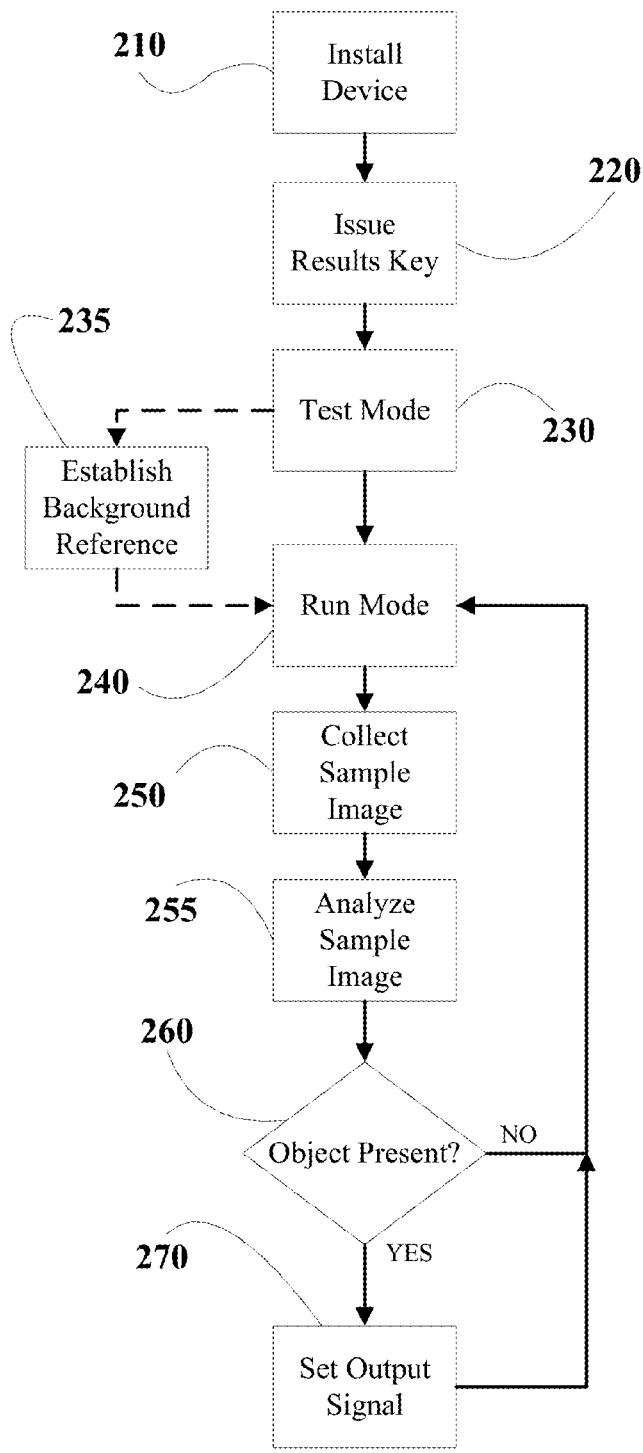
FIG. 4 is a schematic block diagram of an example embodiment of the operation of the image capture and processing device operating in cooperation with the Results Key.

As provided in the example process flow of FIG. 4, issue Results Key 220 follows install device 210. This representative process example is given for illustrative purposes only and it should be noted that the order of 210 and 220 as given in FIG. 4 are interchangeable. It is expected that for generic applications, step 220 will proceed to step 210 and actually occur at 160, while custom implementations will follow the process flow as given in FIG. 4. Furthermore, new or improved Results Keys 20 will become available following installation of the image capture and processing device 30 and revised Results Keys 20 may be issued to installed devices at a future date.

As will be obvious to one skilled in the art, there are many ways to issue a Results Key 220. As previous disclosed, Results Keys 20 are typically referred to as a software module, whether limited to the analysis data set or inclusive of the operating system. The methods well known in the art for transferring or making software available from one hardware platform to another, remote platform are incorporated herein by reference and include such transfer techniques as directly programming memory chips, transfer of software by electronic cable interconnect, or by wireless transmission using any frequency in the electromagnetic spectrum. The preferred embodiment however, is for the Results Keys 20 to be made available to the image capture and processing device 30 through the use of programmable memory cards, for example, SD cards, which are solid-state electronic data storage devices used with digital cameras, handheld and mobile computers, telephones, music players, video game consoles, and other electronic devices. These memory cards, including their companion technology used primarily for Personal Computers called memory sticks or "USB FLASH", are available in a wide variety of packages with varying electrical interconnect formats and offer high re-record-ability, power-free data storage, small form factor, and rugged environmental specifications. There is also a variety of different memory technologies used as well, with the most popular technology employing a form of FLASH memory. Also contemplated by the present system are the use of magnetic and optical storage technologies, which are less desirable given the complexities of the read/write hardware mechanisms required to employ them.

Issuing the Results Key 220 also incorporates well known security for the transfer of software/firmware from one platform to another. Password protected access, encryption, private/public key pairs, digital signatures and hashing algorithms are used in an appropriate manner to provide the desired level of security for a particular deployment application.

Issuing the Results Key 220 necessitates that the image capture and processing device 30 has the ability to accept power and achieve an operating state that allows the transfer of data and/or a software module. This requires the image capture and processing device 30 to complete an initialization process as is common to electronic devices and either moves automatically or through user commands to a state that will facilitate the transfer of information. There are numerous tasks that can be completed as part of the initialization process including self test, power monitoring or inventory of available functions. Regardless of the order of 210 and 220 or the method used to issue the Results Key 20, the outcome of step 220 is that the software module that includes the Results Key 20 is stored within the image capture and processing device or, the media used to supply the Results Key 20 becomes an operational memory component of the image capture and processing device 30. This process also includes authentication of the transfer media. Following completion of 210 and 220, the device is effectively initialized.

Step 230 is a preferred, yet optional, step and proves to be useful for most applications using the present system. In its most basic functional embodiment, test mode 230 exercises the image capture and processing device 30 using the installed Results Key 20. The test mode 230 state can be entered into automatically as a gating state as part of the device initialization process or it can be activated using a mechanical switch or remotely activated. Some advantage may be gained by utilizing a mechanical switch or remote activation as the test mode 230 state can be activated without requiring re-initialization of the device to enter the test mode 230 state as would be required for automatic entry into the test state. When in test mode 230, the image capture and processing device outputs a signal 275 indicating recognition of the object of interest 265 when the object is placed in the field of view. While the preferred approach is for actual objects of interest 265 to be present in the field of view 253 to verify system operation, this may not always be practical. Sample images, models or other methods used to develop the Results Key 20 can be used to trigger output signal 275. Test mode 230 is not required to operate identically to run mode 240 as it may be advantageous to limit functionality of the image capture and processing device 30 and/or the Results Key 20 to simplify the system verification process. For example, any shadow requirements contained in the Results Key 20 may be disabled such that a picture of the object of interest 265 can be placed in the field of view 253 to generate output signal 275. Another example of an operational difference between test mode 230 and run mode 240 may be the length of time that the output signal 275 remains activated. While there is no limit for the time the output signal 275 remains active, an intended application for which the image capture and processing device 30 is deployed may require the output signal 275 to remain active for five (5) minutes or even an hour, for example, and this may unnecessarily extend the time required for system verification. Test mode 230 may incorporate a different time for the output signal 275 to remain active to facilitate a large number of sample objects of interest 100 in a shorter amount of time. Other differences exist as will be obvious to one skilled in the art. Obviously, any functional limitation present during test mode 230 reduces the level of verification such that the preferred approach is for the device to operate identically to run mode 240.

If test mode 230 is entered automatically as part of the system initialization process, it moves to the next operational state after a prescribed amount of time or number of recognition cycles. If test mode is entered manually through the use of a switch or remote activation, the switch is set to the next operational state or is remotely activated to the next state. Other operational states are contemplated, such as an image or data collection state. Image or data collection states can be used to collect images and data from the deployment location of the image capture and processing device 30, which can then be used to tune or optimize Results Keys 20. The foregoing steps of FIG. 4 are provided for illustrative purposes and are not intend to establish limitations of the present system. These are all precursors however, to the image capture and processing device 30 reaching the run mode 240 state.

Also shown in FIG. 4 is the optional path to establish a background reference 235 that may be used for processing when the image capture and processing device 30 is in run mode 240. Once the image capture and processing device 30 is installed in its deployment location, certain application will have a view of a static field of view 253 that remains relatively constant over time, which is generally referred to as the 'background'. During the run mode state, which includes 240 through 270, the background can be "subtracted" for the collected sample images 250, resulting in only the changes from the reference version captured in 235 remains. This is an extremely advantageous feature as it quickly determines whether additional processing is required. As part of the device initialization, this constant background can be recorded by the image capture and processing device 30 and stored internally. The preferred approach is for the background to be captured when the device is in test mode 230 but it can be recorded in other parts of the device operation if desired. If fact, the background reference can be 're-calibrated' while the device is run mode 240 as describe below.

The background reference established in 235 is used by steps 240 through 260 to aid in the processing and analysis of sample images collected in 250. This requires the reference background to remain identical to the background that is part of the sample image in 250. A great deal of time may elapse between the time the reference background is captured and stored 235, and the time when a sample image 250 is captured at some point in the future. This elapse time may result in the background changing or the environmental conditions may change the background as well, such as wind blowing through the trees. The present system accommodates a fair amount of variability between the reference background 235 and the sample image background 250. Subtle changes in the background result in characteristic 'noise' in the analysis portion of the process and can be filtered using well known techniques for image processing. Further, if 'noise' is consistently present in the results of sample image processing, the image capture and processing device can initiate a re-calibration capture of the reference background 235. There are limits to this self-correcting process naturally, and at some point the device may need to be re-initialized.

Run mode 240 establishes a processing loop that includes steps 240 through 270. Run mode 240 is the operational state where the image capture and processing device 30 captures an image 250, analyzes the image 255 by executing or accessing the Results Key 20 to determine if the object of interest 265 is present, activates the output signal 275 if the object is present and repeats the processing cycle. There are many variations of this processing loop as will be obvious to one skilled in the art and steps 240-270 should be regarded as illustrative only. The order of the steps are easily rearranged and in fact, may all operate simultaneously as is common for multi-threaded or task stack operating systems such that no distinct beginning or end of each is apparent. Steps 240 through 270 are simply used to illustrate the claimed method of analyzing captured images based on a remotely defined set of criteria contained in the Results Key 20.

Sample images collected in step 250 are captured from the field of view 253 using the image capture and processing device 30 and are captured with a high degree of flexibility that is managed through setting several different parameters. The rate at which images are captured, typically referred to as the sample rate, or sampling frequency, is driven by many different parameters that includes, but is not limited to, image resolution, efficiency of the analysis, processing power, expected velocity of the object of interest 100 and requirements of the deployment application. In one alternate embodiment, captured images can be stored and retained by the image capture and processing device 30, either all images captured or only the ones determined to contain the object of interest 265, which can also impact the sample rate. The sample rate can also vary within a given deployment application and need not be constant. Given the detection or determination of certain condition in one or more sample images, the sample rate can be changed to speed up or slow down as be appropriate to support determining whether the object of interest 265 is present or not. Motion of an object of interest is a powerful component for imaged information that can used to recognize or determine the presence of an object of interest 265 and the sample rate can be varied to optimize the information in successive images as described below. In the extreme point, the sample rate approaches or achieves that of video, which typically begins above 20 frames per second with a variety of formats used in practice. While the effect of raising the sample rate to one that is typical of video creates the appearance of fluid motion when viewed by the human eye, the sample images are still individually analyzed in step 255. In the instance of the present system, the sample rate is just a tool to optimize the efficiency of the overall system performance.

Sample images of step 250 may be collected in any lighting conditions, including capturing images in the dark for both indoor and outdoor applications. Digital image processing provides a variety of tools for adjusting and correcting images within a wide range of ambient light conditions and these processing techniques can be included in the Results Key 20 to minimize any modification requirements for the image capture and processing device 30. There are a variety of alternative embodiments possible however, that can extend the ability to collect a suitable sample image 250 for analysis in step 255.

The addition of low power Light Emitting Diodes (LED) that irradiates the field of view 253 provides sufficient low light illumination to allow the capture of suitable sample images 24 hours a day for both indoor and outdoor applications. Recent advances in LED technology have increased the watts per lumen ratings for white light LEDs while keeping the power consumption low. If an 'always on' LED light is undesirable, filtering can used for the imaging component (314 and 318) of the device 30 to allow it to capture images in the near infra-red region of the electromagnetic spectrum, allowing the image capture and processing device 30 to 'see in the dark'. This approach can be further enhanced by the addition of infra-red LEDs to illuminate the field of view 253. Further modification to the image capture and processing device 30 can include the use of Passive Infra-Red (PIR) sensors 342 that detect and image thermal radiation emitted by bodies. Thermal quantification 140 of objects of interest 100 is a viable recognition approach and easily supported by the example process outlined in FIG. 3 used to produce the Results Key 20. Other techniques for imaging objects in low light conditions that are well known in the art are possible as will be recognized by one skilled in the art and those techniques are incorporated herein by reference.

In the preferred embodiment, the collected digital sample image 250 is placed in a temporary memory 326. There are many different means to store electronic information and all are incorporated herein by reference and include such methods as magnetic, optical, ferro-electric, FLASH, etc. as will be familiar to one skilled in the art. The electronic memory contemplated for the preferred embodiment of the present system is the type optimized for fast read/write cycles such as electronic memory that is prevalent in the digital camera industry. For most deployment applications, the sample image 250 is discarded, erased or overwritten so that no lasting record is maintained. As previously disclosed, some deployment application may require some or all images to be retained. While compression algorithms are very efficient, retention of all sample images is likely to be limited to only highly specialized deployment applications as the cost and size of the amount of memory required for generalized deployment application would quickly become burdensome. A more practical situation for image retention is that only images that cause activation of the output signal 275 would be retained. These deployment applications are likely to be ones that require more interactive monitoring given the sensitivity of an object of interest 265 coming into the field of view 253. Storage and retention of images is accomplished either through storage in some internal memory 322 of the image capture and processing device 30, through an external memory card inserted into the image capture and processing device 30 (preferred), a cable interconnect or through wireless transmission. The preferred embodiment, however, discards the image after completion of analysis 255 to minimize the amount of memory and cost of the image processing and capture device 30. This approach also allows the use of Random Access Memory (RAM), which is typically faster than memory that maintains information in the absence of power (e.g. FLASH memory). For purposes of this illustrative discussion, collecting sample image 250 is complete when a sample image is placed in temporary memory 326. The arrival of a new sample image in the temporary memory 326 triggers a control signal to initiate step 255, which analyzes sample image.

Analyze sample image 255 is where the Results Key 20 is applied to the sample image 250 to determine if the object of interest 265 is present. The analysis process may utilize one or more Results Keys 20, for example, where the use of one Results Key 20 triggers sequential use of another. Thus, an object speed analysis outcome, as discussed above, may trigger further discrimination to assess whether the object is a car or motorcycle. Alternatively, the identification of two automobiles approaching one another on a road may trigger a search for interaction between the automobiles, such as a collision. Alternatively, the respective Results Keys 20 may be merged as one. As previously disclosed the data contained in the Results Key 20 ranges from flat file passive information used by the software/firmware resident within the image capture and processing device 30, to discrete executable software modules that are launched by the image capture and processing device operating system. It is likely the Results Key 20 contains a combination of flat file information used to 'configure' the image capture and processing device (sample frequency, time for active output signal, etc.) and executable software modules (functions and/or algorithms) used to analyze the image. Regardless of the approach, the sample image 250 is processed in cooperation with the Results Key 20 to detect, determine or otherwise recognize whether the object of interest 265 is present within the sample image based on criteria provided by the Results Key 20. At the completion of step 255, the outcome of the analysis step 255 can be as simple as "true" (object of interest present) or "false" (object of interest not present). This outcome is supplied to logic function 260 that either sets the output signal 270 if true or initiates a new processing cycle. Given a true or positive outcome of 255, and the logic function 260 sets the output signal in 270, a new processing cycle is initiated. The foregoing description is provided at the most elementary level and has many alternative embodiments that accomplish the identical means of using the output of one process to drive conditional response in another process as will be recognized by one skilled in the art.

The present system also includes methods to minimize or prevent 'spoofing' the image capture and processing device into incorrectly setting output signal in 270, or not setting output signal 270 when the object of interest is present. The simplest example of incorrectly setting the output signal 270 is if a 2-dimensional picture of the object of interest were placed in the field of view 253. Image analysis techniques are available for "shadow analysis", where the shadows of objects can be detected and quantified. Shadows cast by objects of interest 265 can be compared to shadows cast by background object to minimize spoofing. These same or similar techniques can be used for the inverse spoofing condition, where the output signal 270 should be set but it is not due to some nefarious act in the field of view 253.

Additional alternative embodiments exist for conditional control of the output signal 270.

One alternative embodiment includes multiple analysis processing loops using steps 240 through 265 to process multiple sample images to recognize the object of interest 265 before setting the output signal 275 in 270. This embodiment serves to increase the level of confidence that the object of interest is, in fact, within the field of view 253. The number of consecutive true or positive outcomes from 255 that are required before 260 sets the output signal is governed by information in the Results Key that configures 260 for the desired number of positive recognition processing loops. Another alternative embodiment involves changing the sample rate given a true outcome from 255. One example of this embodiment is where the sample rate is maintained at a relatively slow rate to conserve power until an object of interest 265 is detected, which causes the sample rate to increase to generate a 'burst' of samples to confirm the object is present. Until the prescribed count of positive outcomes is achieved, the output signal 275 is not set in 270.

Another alternative embodiment is where 255 exercises only a limited amount of processing functions until a change is detected in the field of view 253, whereby additional processing is activated in subsequent analysis loops 240 through 265. For example, if the optional reference background 235 is employed when the image capture and processing device is initialized, sample images are 'subtracted' from the reference background 235 to identify a difference in the field of view 253. This process is very efficient and fast, consuming the minimum amount of power and processing time. If the result of the subtraction is non-zero, meaning something is different, additional processing is enabled by 260 for subsequent processing loops using steps 240 through 265. Only until the outcomes of 255 met the criteria established by the Results Key 20 does logic function 260 set the output signal 275 in 270.

Motion has been referenced herein as a powerful tool for determining the presence of an object of interest 100/265. Employing motion as a property for detection requires multiple analysis processing loops where information concerning the present loop is retained and used for subsequent loops. Here, the position of the suspected object of interest 265 is tracked over multiple sample images 250 and this positional information is used by the Results Key 20, in conjunction with other information from the outcome of 255 to reach the level of confidence before the output signal 275 is set in 270. For example, the centroid of a feature within the suspected object of interest 265 is identified in successive images and its displacement in the field of view 253 is measured. Coupling the change in displacement with an internal timer or Real-Time Clock 338 incorporated in the image capture and processing device 30 as disclosed below, allows the speed, velocity or acceleration to be computed.

Another alternative embodiment is where more than one object of interest 265 must be within the field of view 253 or the object of interest 265 is present plus an additional event occurs or, two or more objects of interest 265 are in the field of view and an event occurs that involves the objects. Examples of these situations include: a car pulling into a driveway AND a person is recognized after detecting the car (somebody gets out of the car); a person is recognized in the field of view AND the person raises in elevation after the initially detected (somebody starts climbing a fence), and; two or more people are detected and the objects merge together (possible abduction of one person by another). These simple examples are but a few of the infinite conditional scenarios that are possible as will be recognized by one skilled in the art and are provided for illustration purposes. The present system provides great flexibility to be configured using the Results Key 20 for just about any scenario.

A further alternative embodiment includes the use of other sensor technologies in conjunction with the present system. There is a wide range of technologies used to measure a variety of properties, and include; motion, sound, distance, acoustic, proximity, infra-red, light, temperature, pressure and flow rates of gases and liquids. By combining one or more of these sensors 342 used to measure the aforementioned properties with the present system, the functional range of the present system can be extended as one or more of these properties provide additional information about the object of interest 100/265 and/or information about the field of view 253. Further, the addition of information for one or more properties can serve to improve the accuracy of the recognition of the object of interest 265 and/or elevate the level of confidence that the object of interest 265 is within the field of view 253.

Information regarding the time of day or location can also be used in combination with the present system. Integration of a Real-Time Clock (RTC) 338 functions within the image capture and processing device 30 can be used to specify the time of day and the Results Key 20 would indicate time windows or a range for which an object of interest 265 would be considered valid. For example, an application may only be interested in objects of interest during dusk from 4:00 pm to 7:00 pm. The RTC 338 can be used to account for a change in light condition, either indoor or outdoor, or even the time of year to account for seasonal changes for outdoor applications. Characterization of the object of interest 120 can include probability of detection based on time of day, weeks, months or years. Location or orientation of the image capture and processing device 30 can also be used to detect objects of interest and advantages are gained by the incorporation of a Global Positioning System (GPS) 334 component within the image capture and processing device 30. Once the image capture and processing device is mounted in its deployment location, the latitude and longitude can be used as information component as specified in the Results Key 20.

Thus far the disclosure has contemplated the most basic configuration of the image capture and processing device 30, minimizing the hardware components which typically drive unit product costs to disclose a novel, low cost image-based sensor. The present system contemplates more complex configurations however, which have a higher unit product cost but a higher degree of functionality, utility, performance and accuracy. One or more property sensors 342 as referenced in the preceding paragraph can be integrated directly into the image capture and processing device 30 and coupled to the processing function (FIG. 4) of the device to deliver increased utility. The presence of one or more property sensors 342 integrated into the image capture and processing device is incorporated into the construction of the Results Key 20 and the information provided by the sensor 342 is used appropriately in 120, 130, 140, 250, 255 and 260. For example, if for a particular deployment application, the ambient temperature is relevant to determining the presence of the object of interest 265, a temperature sensor is incorporated into the image capture and processing device 30. With this hardware configuration, 120 would include a characteristic temperature requirement and 250 would sample the ambient temperature and supply this information, along with the sample image 250 to step 255 for analysis. One skilled in the art will recognize the huge range of possible permutations and combination of property sensors 342 with the present system and the functionality that is possible to improve the overall performance objective of recognizing an object of interest 265 with a high degree of confidence.

One simple example implementation of the forgoing discussion on combining property sensors 342 with the present system is where the deployment application is to detect the presence of an automobile pulling up in a driveway. The addition of a microphone 342 to the image capture and processing device 30 would allow the measurement of sound coincident with collecting a sample image 250 with sound levels specified in the Results Key 20. Clearly, the addition of a sound measurement in 255 elevates that level of confidence that an automobile is present in the field of view when coupled with the outcome of the image analysis 255.

The present system has thus far disclosed only a passive monitoring of the field of view 253 but active monitoring is also contemplated. Active monitoring includes the incorporation of signal emitting components 346 in the image capture and processing device 30 that provide additional function range, utility, performance and accuracy. Complex combinations of property sensors 342, signal emitting components 346 and imaging components 314/318 are possible to drive the occurrence of false-positive or false-negative outcomes to nearly zero. For example, consider the following hardware configuration for the image capture and processing device 30: Two imaging components 314/318, one with a visible light filter (for near infra-red imaging) and one with an infra-red filter (for visible light imaging); Two sets Light Emitting Diodes (LEDs) 346 directed toward the field of view, one set emits visible light frequencies, the other set emits infra-red frequencies, and; a Passive Infra-Red sensor (PIR) 342. This hardware configuration is supported by the process and method given in FIG. 3 such that Result Keys 20 can be produced that manage the various components to operate harmoniously to detect the object of interest 265 with near certainty. This example hardware configuration operates in any lighting conditions with an error detection rate that approaches zero, as will be recognized by one skilled in the art.

Figure 5:
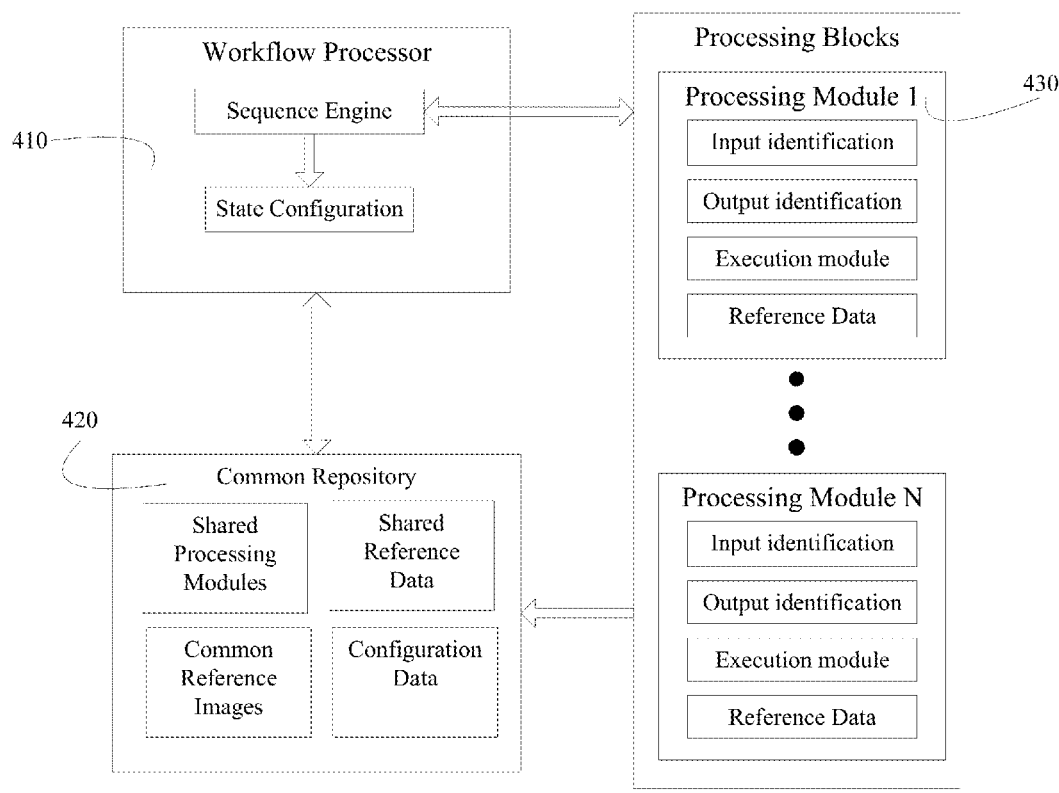
FIG. 5 shows a Results Key according to one embodiment.

By way of nonlimiting example, one possible data structure for the Results Key 20 is shown in FIG. 5. The Results Key 20 data structure contains, generally, a set of code blocks to provide workflow management, data storage and processing functions. A workflow processing code block 410 coordinates the execution of the processing block 430 while utilizing information in the common repository 420. The workflow processor 410 uses state configuration information to determine the order of execution for the processing block 430. Processing block 430 consists of N number processing modules that supply various algorithms, functions and/or operators that perform specific functions to manipulate images. A sequence engine provides the processing block 430 with data needed to perform a specified operation by an individual processing module. The identification of the input data is described in each processing module and the input data may be provided by the common repository 420, another processing module or components contained in the image capture processing device, including the RTC 338 or property sensor 342, for example.

Each processing module executes a unit of processing work on a defined input to produce a defined output as shown. The processing module may contain executable code and may include the execution of other processing modules in the processing block or a shared processing module contained in the common repository 420. The processing modules operate on data provided by the workflow processor 410 and data accessed by the processing block 430 from the common repository 420.

Each processing module 430 has input identification information regarding the data it requires for performance of its specified operation and is accessed or read by the workflow processor. The input identification information identifies the type and characteristics about the data. For example, the input identification may define that raw camera input at 300 dpi in grey scale format. Each processing module 430 also includes an output identification that describes the output produced by the module, which includes the type and characteristics of the data. For example, the output identification may produce an image with the definition of the detected edges of an object of interest 265.

There are many different data structures possible for the Results Key 20 as will be recognized by one skilled in the art and the foregoing discussion is for illustrative purposes only. This example shows one possible approach for organizing the Results Key 20, which generally contains image analysis functions, configuration data, static parameters and the computer code necessary to manage the foregoing and the hardware device. There is no requirement to separate the contents into blocks as there is no limitation on the number of blocks of code that can be used.

Fall Detection

Studies have shown that people have predictable movements and/or postures associated with getting out of bed and these movements vary with age. The majority of these studies have been produced for physical therapy purposes to help rehabilitate elderly patients. Characteristic movements and postures are broken into head and trunk, far arm, near arm and legs. The categories each contain descriptive movements or positioning for each method used to get out of bed. The present instrumentalities is trained to detect the categorical movements and postures for one or more body parts to provide health care professionals advanced warning that an at-risk patient is about to attempt to get out of bed. Additional research has shown that medical or physiological conditions result in characteristic movement indicating that an attempt to get out of bed is imminent, such as the need to go the bathroom. The present instrumentality detects these patient movements, which provides a sufficient warning period for care givers to respond. The inverse information is also beneficial for health care professionals, which is lack of patient movement and can be monitored, measured and tracked for different applications.

Figure 6:
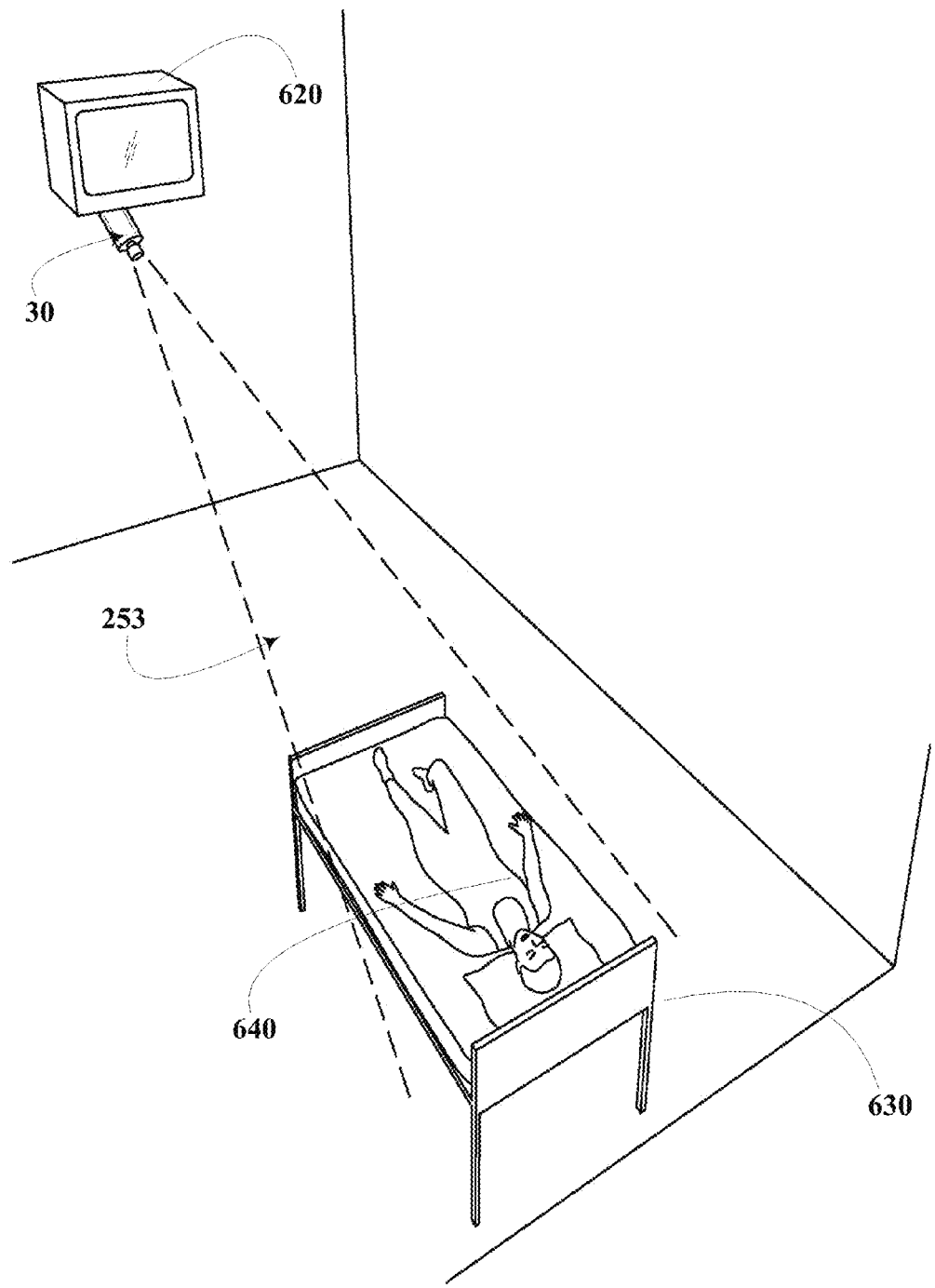
FIG. 6 provides a popular sequence of positions and postures used by elderly persons when getting out of bed.

The image capture and processing device 30 is typically mounted in an elevated position within a monitored room but elevation is not required, but preferred. As shown in FIG. 6, an advantage of most institutional health care rooms are that televisions 620 are in every room and mounted high on the wall opposite of the foot of the bed 630. This consistent location is an ideal placement for the image capture and processing device 30, which is trained to detect and classify specific movements or postures of patients 640 from above the bed.

Figure 7:
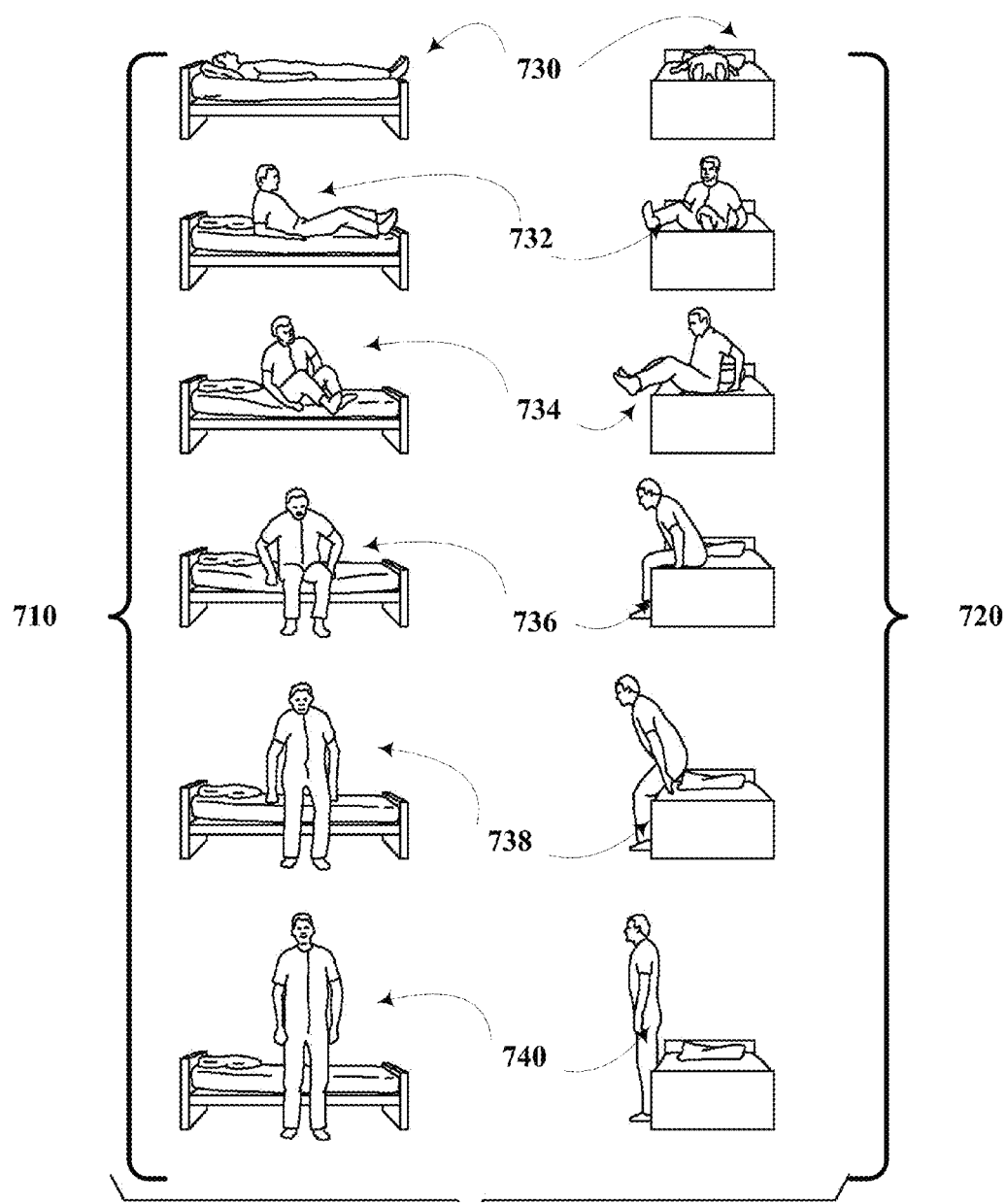
FIG. 7 shows possible deployment configuration for the patient observation image capture and processing device.

There are many scientific studies that have categorized human movement as it relates to certain, specific tasks. The present disclosure takes advantage of the availability of these studies to train specific algorithms for recognizing when a patient is attempting to get out of bed. For example, a published research report, titled "Age Differences in Movement Patterns Used to Rise from a Bed in Subjects in the Third Through Fifth Decades of Age" Physical Therapy/ Vol. 73, No. 5, May 1993, included a pictorial representation of the most common movements and postures used to get out of bed as given in FIG. 7. FIG. 7 shows a side view 710 and an end view 720 of the most frequent movement pattern used to get out of bed by 50-to-59-year-old subjects. Postures 730, 732, 734, 736, 738 and 740 map the progressive body movement used to get out of bed. These postures, which is inclusive of all intermediate postures that occur between those given in FIG. 7, can be used to recognize an individual is getting out of bed. The image processing algorithms used to recognize these movements are generally available in the public domain and include techniques such as blob tracking, Histogram Of Gradients, Support Vector Machines, facial recognition, Motion History Images, etc. and are used to process training imagines into one or more numerical representations that is independent of the training images and creates the Results Key to provide the desired output signal. Training consists of a large set of sample data for both positive and negative images in the field of view. The training images are processed in mass by one or more algorithms to generate a numerical representation of the consistent features present in training images, i.e. the Results Key. The training process severs all links or traceability between the training images and the output numerical representation such that the Results Key is independent of any image representation or database storage location(s). When the Results Key is deployed remotely to the image capture and processing device, sample images are captured from the field of view, processed by the same algorithms used to create the Results Key and a numerical outcome is generated. The numerical outcome of the processed sampled image is then overlaid on the Result Key to determine if the outcome of the sampled image is within the boundaries created by processing the training images. If the sampled outcome is within the boundaries, the output signal is generated. Another advantage of the present system is that by training it to detect and/or recognize patient postures or the positioning of body parts, the system is able to perform its functions using discrete images or video taken of the field of view with very low frame rates, such as one (1) frame per second. This minimizes the amount of microprocessor power required to keep the overall hardware inexpensive and forces the algorithms to be very efficient.

One embodiment has sensitivity settings that are used to tailor the monitoring for a particular patient. The least sensitive setting provides an alarm signal when a patient exhibits motions that are attributable to an effort to get out of bed. Characteristic movement patterns include a combination of trunk, arm and leg movements that are used to get out of bed.

The most sensitive setting provides an alarm for any patient movement. Intermediate sensitivity settings will be determined through additional research and likely will include other characteristic movements and the measurement of sustained periods of restlessness or fidgeting.

In one aspect, a patient observation device may have several modes of operation depending on the patient needs and can be configured using well known methods that are common for electronic devices; cabled or wireless interconnect using standard interface protocols or button activation. The preferred approach is a wireless interconnect to minimize physical cabling or the need to be able to physically access the device when mounted in position. The interconnect for the alarm or notification function capitalizes on the well documented means of interfacing with existing health care facility infrastructure for communicating alarms or notifications. Examples of this well known art are given in U.S. Pat. No. 7,746,218, Collins, Jr. et al and Beggs '293. Another mode of operation is where escalating or multi-tier alarms are used to communicate the status of a patient without needing to view an image or physically be present for observation. The alarm modes can be programmatically set where the most sever situation is assigned the loudest or persistent alarm mode.

The patient observation device optionally also has a timer that is used for a number of different functions. One use of the timer is to measure the amount of time a patient remains in a relatively identical position. Patients who spend long periods of time in bed must be periodically moved or re-adjusted to prevent the occurrence of pressure sores or more commonly known as bed sores. The patient observation device is able to track body position and is trained to recognize or detect a minimum amount of positional change that is necessary to change pressure points on the body for proper circulation. The caregiver can set the patient observation device to alarm if the patient does not voluntarily re-position within a certain amount of time so that the caregiver can come in and require re-positioning. An advantage of an image-based approach to monitor this situation is that the patient observation device is not at risk of being out position due to patient movement as is common for existing monitoring methods.

The timing function may also be used to create a statistical assessment of movement by a patient. If, for example, a patient exhibits five voluntary position adjustments within a 15 minute interval, this may be indicative of discomfort or a predictor of a likely attempt to get out of bed.

Another drawback of previous bed monitoring systems is that when a caregiver arrives at the bed side to tend to a patient, he or she must remember to disable the monitor otherwise a false alarm will be generated as the patient moves around or re-adjusts as is often the case when visitors arrive. The converse is also true when the care giver is done, he or she must remember to re-activate the monitor prior to leaving the bedside. Today's health care professionals are overwhelmed with monitors and alarms in patient's rooms and bed monitors are one more system to manage. The present disclosure provides a significant improvement over this situation by automatically disabling the alarm or notification function when a caregiver or other visitor arrives at the patient's bed side. Since the present instrumentality is trained to recognize human movement, it is also trained to recognize there is more than one human in the field of view. Further, the trained algorithms can distinguish that one person is standing and one remains in bed. This capability can be extended to integrate the situation where one or more caregivers arrive at the bedside, assist the patient out of bed and the patient is absent for some period of time, for example, to go to the bathroom or attend some other appointment away from the bed. The present system and method is able to track this situation and recognize it is not an attempt by the patient to get out of bed unassisted.

The present state of health care has a heightened awareness and sensitivity toward patient privacy, which includes picture or video footage captured during the patient's care at the facility. Another advantage of the present instrumentality is that it protects the privacy of the patient as there are no images of patient saved or communicated to other systems. The utility of the system does not require images to be saved and thus creating a 'medical record', which then becomes subject to Health Insurance Portability and Accountability Act (HIPAA) requirements that govern the privacy and security of an individual's health information.

Previously disclosed bed monitoring systems claimed to be able to detect patient motion. The systems and methods are based on the use of a pad that is positioned under a patient and the pad consisted of a matrix of switches. When these systems detected 'movement', it is limited to identifying that different switch closures have been detected. This situation provides only two dimensional data that prevents identification of the type of movement and therefore adds no information to determine if the patient is trying to get out of bed or just turning over. The present instrumentalities allow three dimensional categorization of movement to identify the motion as part of the pattern used by patients to get out of bed, thus enabling the present system to issue an alarm or notification at the earliest possible time.

Figure 8:
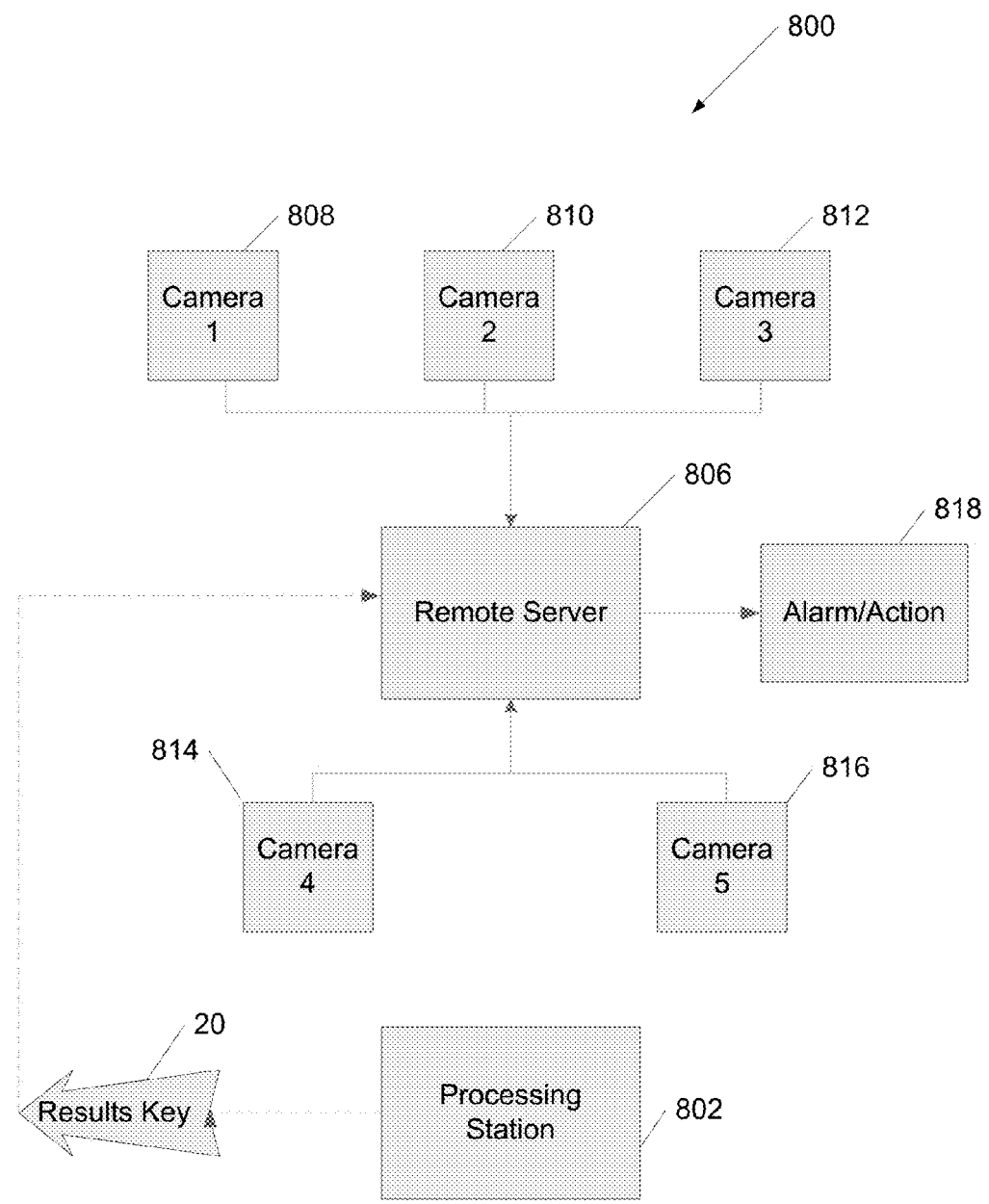
FIG. 8 shows an alternative embodiment including a standalone processor that is configured to receive video signals from a plurality of cameras.

FIG. 8 shows an alternative embodiment as system 800 where a first processing station 802 creates a results key 20 as discussed above. The results key 20 is provided to. a remote hardware configuration shown as remote server 806 which includes operational software deployed to a remote computer server communicating with multiple image capture devices, such as cameras 808, 810, 812, 814, 816. In this embodiment, the remote server 806 possesses sufficient computer processing power to allocate a functioning Results Key processing chain to each of the input signals from the connected image capture devices. It will, be appreciated, for example, that each of the cameras 808-816 may reside in a hospital room or long term care facility where the system 800 monitors patient movements as described in context of FIG. 7 to ascertain when patient movements are placing the patient at increased risk of having a fall. Once system ascertains this risk, it generates an alarm or other action 818 indicating a need for possible intervention by health care staff. It will be appreciated also that more than one of cameras 808-816 may reside within a particular room and that these cameras may be positioned to capture different perspectives of the same patient to increase the accuracy of fall prediction. Each perspective may be accompanied by its own separate results key 20, and so it is possible to have parallel processing from different perspectives to predict the same event, i.e., the risk of a patient having a fall. Those skilled in the art will understand that the preferred embodiments, as hereinabove described, may be subjected to apparent modifications without departing from the true scope and spirit of the invention. The inventor, accordingly, hereby state his intention to rely upon the Doctrine of Equivalents, in order to protect his full rights in the invention.

What is claimed is:

1. A method of image processing, comprising the steps of:
   constructing a results key at a first processing station by use of image processing algorithms operating upon a plurality of images representative of different human individuals to produce the results key as a data set that contains sufficient information to identify a human being as an object of interest with a statistical level of certainty accommodating various shapes and sizes of human beings;
   making the results key available to a central computer system that includes at least one image capture and processing device remote from the first processing station, where the image capture and processing device is operable to capture an image presented to a field of view of the image capture and processing device; and
   using the results key at a central computer system located remotely from the first processing station to process the field of view image to identify a human being as the object of interest, and to provide an output signal indicating that the human being is present according to parameters established by the results key at a level of analysis indicative of human beings inclusive of various shapes and sizes of human beings.

2. The method of claim 1, wherein the step of making the results key available is performed by using a portable memory component to transfer the results key from the first processing station to the central computer system.

3. The method of claim 1, wherein the step of making the results key available is performed by using a wireless transmission to transfer the results key from the first processing station to the central computer system.

4. The system of claim 1, wherein the step of making the results key available is performed by using a cable interconnect to transfer the results key from the first processing station to the central computer system.

5. The method of claim 1, wherein the step of constructing the results key includes using data from one or more physical property sensors to enhance the level of statistical certainty.

6. The method of claim 5, wherein the image capture and processing device further includes one or more physical property sensors configured to provide property sensor output, and the step of using the results key includes use of the physical property sensor output to facilitate processing of the field of view image.

7. The method of claim 1, wherein the image capture and processing device further includes a real time clock configured to provide a time output signal, and the step of using the results key includes use of the time function output signal to facilitate processing of the field of view image.

8. The method of claim 1, wherein step of using the results key includes providing the output control signal based upon observed interaction over time between a plurality of discrete objects of interests.

9. The method of claim 1, wherein step of using the results key includes changing a sampling rate of the field of view image based upon a detected event.

10. The method of claim 1, wherein the step of providing the results key includes updating the results key with an improved results key, where the improved results key provides a higher degree of statistical certainty for identification of the object of interest.

11. In an image capture and processing device that detects human movements, the improvement comprising:
    a processor configured to operate upon image data to ascertain human movements by application of a results key as a data set that contains sufficient information to identify in the image data set a human being as an object of interest with a statistical level of certainty accommodating various shapes and sizes of human beings;
    means for analyzing the human movements to ascertain specific movements related to at least one action selected from the group consisting of characteristic movement patterns that are defined by parameters provided by the results key; and
    means for providing an output signal when the specific movements occur in the field of view.

12. The image capture and processing device of claim 11, further including a remotely monitored data display unit configured to display an alarm upon receipt of the output signal.

13. The image capture and processing device of claim 11, wherein the means for analyzing includes an artificially intelligent algorithm that is trained to detect the specific human movement.

14. The method of claim 1 further comprising a step of performing an analysis of specific human movement occurring in the field of view.

15. The method of claim 14, wherein the step of performing the analysis includes an analysis to ascertain movement consistent with a human getting out of bed.

16. An image capture and processing device, comprising:
    an imager configured to capture image data representative of an image presented to a field of view of the image capture and processing device, and
    a computer system with data storage that contains a results key as a data set that contains sufficient information to identify a human being as an object of interest with a statistical level of certainty accommodating various shapes and sizes of human beings,
    the computer system being configured to receive the image data from the imager and to process the same by applying parameters established by the results key to identify a human being as the object of interest, and to provide an output signal indicating that the human being is present according to parameters established by the results key at a level of analysis indicative of human beings inclusive of various shapes and sizes of human beings.

17. The image capture and processing device of claim 16, wherein the computer system is configured to provide an analysis of specific human movement occurring in the field of view.

18. The image capture and processing device of claim 17, wherein the analysis includes an analysis to ascertain movement consistent with a human getting out of bed.

19. The method of claim 1, wherein the step of using the results key includes passive imaging of the field of view.

* * * * *